US012636457B2

(12) United States Patent (10) Patent No.: US 12,636,457 B2

Tebbutt et al. (45) Date of Patent: May 26, 2026

(54) HEADGEAR FOR RESPIRATORY THERAPY

(71) Applicant: Fisher & Paykel Healthcare Limited, Auckland (NZ)

(72) Inventors: Adam Alexander Tebbutt, Auckland (NZ); Paul Mathew Freestone, Auckland (NZ); Mark Richard Tomlinson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 727 days.

(21) Appl. No.: 18/002,021

(22) PCT Filed: Jun. 15, 2021

(86) PCT No.: PCT/IB2021/055240

§ 371 (c)(1),
(2) Date: Dec. 15, 2022

(87) PCT Pub. No.: WO2021/255626

PCT Pub. Date: Dec. 23, 2021

(65) Prior Publication Data

US 2023/0211106 A1 Jul. 6, 2023

Related U.S. Application Data

(60) Provisional application No. 63/040,438, filed on Jun. 17, 2020.

(51) Int. Cl.
A61M 16/06 (2006.01)

(52) U.S. Cl.
CPC .... A61M 16/0683 (2013.01); A61M 16/0611 (2014.02)

(58) Field of Classification Search
CPC .......... A61M 16/0683; A61M 16/0611; A62B 18/02; A62B 18/025; A62B 23/02; A62B 23/025
See application file for complete search history.

(56) References Cited

U.S. PATENT DOCUMENTS

| | | | |
|---|---|---|---|
| 9,032,955 B2 * | 5/2015 | Lubke | A61M 16/0605 128/206.21 |
| 2008/0190432 A1 | 8/2008 | Blochlinger et al. | |
| 2009/0044808 A1 * | 2/2009 | Guney | A61M 16/0622 128/207.18 |

(Continued)

FOREIGN PATENT DOCUMENTS

| | | |
|---|---|---|
| FR | 1450883 | 6/1966 |
| WO | 2006130903 A1 | 12/2006 |

(Continued)

OTHER PUBLICATIONS

International Search Report for Application No. PCT/IB2021/055240 dated Oct. 1, 2021.

*Primary Examiner* — Valerie L Woodward
(74) *Attorney, Agent, or Firm* — VIA LLP

(57) ABSTRACT

Disclosed is a headgear for an interface, comprising a rear loop, a lower side strap extending from the interface to the rear loop, and a pivotable connection. The pivotable connection is located between the lower side strap and the rear loop, or on the lower side strap. The pivotable connection is configured to allow for lateral movement of the lower side strap.

28 Claims, 33 Drawing Sheets

(56)         References Cited

U.S. PATENT DOCUMENTS

2015/0165152 A1* 6/2015 Haibach ............... A62B 18/084
                                                   128/206.21

FOREIGN PATENT DOCUMENTS

| | | |
|---|---|---|
| WO | WO 2012/177152 | 12/2012 |
| WO | WO 2013/026092 | 2/2013 |
| WO | WO 2014/142681 | 9/2014 |
| WO | WO 2017/031263 | 2/2017 |
| WO | 2017158476 | 9/2017 |
| WO | 2018220535 A1 | 12/2018 |

* cited by examiner 140, 240, 340

150, 250, 350

HEADGEAR FOR RESPIRATORY THERAPY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The present invention relates to headgear for respiratory therapy, and particularly headgear for an interface.

BACKGROUND

In patients suffering from obstructive sleep apnea (OSA), muscles that normally keep the upper airway open relax during slumber to the extent that the airway is constrained or completely closed off, a phenomenon often manifesting itself in the form of snoring. When this occurs for a period of time, the patient's brain typically recognizes the threat of hypoxia and partially wakes the patient in order to open the airway so that normal breathing may resume. The patient may be unaware of these waking episodes, which may occur as many as several hundred times per session of sleep. This partial awakening may significantly reduce the quality of the patient's sleep, over time potentially leading to a variety of symptoms, including excessive daytime sleepiness, chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that will reduce the frequency and/or duration of apneas, hypopneas, and/or flow limitations. The therapy is often implemented by using a positive airway pressure device to deliver a pressurized stream of air through a conduit to a patient through a patient interface or mask positioned on the face of the patient.

SUMMARY

According to a first aspect, the present disclosure may broadly provide a headgear for an interface, comprising:

a rear loop, a lower side strap extending from the interface to the rear loop, a pivotable connection, the pivotable connection located between the lower side strap and the rear loop, or on the lower side strap, wherein the pivotable connection is configured to allow for lateral movement of the lower side strap.

In some configurations, the rear loop comprises:

a top strap configured to extend across a top of the user's head in use, a rear strap configured to extend across a back of the user's head in use.

In some configurations, the headgear comprises an upper side strap extending from an interface to the top strap.

In some configurations, movement and/or rotation of the rear strap in a direction away from the interface causes the headgear to enter the donning and doffing configuration.

In some configurations, movement and/or rotation of the top strap in a direction toward from the interface causes the headgear to enter the donning and doffing configuration.

In some configurations, positioning of the interface on a user's face causes the headgear to enter the use configuration.

In some configurations, positioning of the top strap across a top of the user's head, and/or the rear strap across a back of the user's head causes the headgear to enter the use configuration.

In some configurations, in the donning and doffing configuration the pair of lower side straps are located further apart than in the use configuration.

In some configurations, the pivotable connection is a bistable pivotable connection, having a first stable configuration where the headgear is in the use configuration, and a second stable configuration where the headgear is in the donning and doffing configuration.

In some configurations, the headgear comprises an intermediate position, wherein the intermediate position is located between the first stable configuration and the second stable configuration.

In some configurations, the intermediate position is an unstable configuration.

In some configurations, in the intermediate position the distance between the lower side straps is larger than in the first stable configuration and/or the second stable configuration.

In some configurations, a pivotable connection axis of the pivotable connection is located in a direction substantially parallel to the upper side strap and/or the lower side strap.

In some configurations, a pivotable connection axis of the pivotable connection extends in a direction so as to bisect the lower side strap and the upper side strap.

In some configurations, the upper side strap and the lower side strap are substantially symmetrical about pivotable connection axis.

In some configurations, the lower side straps comprise at least one hinging arm, the hinging arm configured to extend behind an ear of the user in use.

In some configurations, the hinging arm extends downwardly from the rear strap.

In some configurations, the hinging arm comprises a preformed twist, wherein an end of the hinging arm located away from the pivotable connection is twisted inwardly.

In some configurations, the rear strap comprises a pivotable connection support.

In some configurations, the pivotable connection support located, in use, between the user and the pivotable connection.

In some configurations, the pivotable connection support providing an area to distribute load generated by hinging.

In some configurations, the pivotable connection is located behind a user's ear in use.

In some configurations, the headgear comprises a pair of upper side straps and a pair of lower side straps, each upper and lower side strap pair being located on each side of the headgear.

In some configurations, the headgear comprises a pair of pivotable connections, each pivotable connection located between the upper side strap and lower side strap of each upper and lower side strap pair, or on the each lower side strap.

In some configurations, the donning and doffing configuration the pair of lower side straps are located closer to the upper side straps than in the use configuration.

In some configurations, the pivotable connection is located at a connection point between the lower side strap and the rear strap.

In some configurations, the pivotable connection is for provided by a hinge.

In some configurations, the pivotable connection is configured to allow for movement of the each lower side strap in a direction upward and downward.

In some configurations, the headgear operable between a first configuration being an in use configuration and a second configuration being a donning and doffing configuration by pivoting of the lower side strap about the pivotable connection.

According to another aspect, the present disclosure may broadly provide a headgear for a respiratory mask, comprising:

two respective pairs of upper and lower side straps, each side strap for connection at a first end to the interface, a top strap configured to extend across a top of the user's head in use, a rear strap configured to extend across a back of the user's head in use, wherein a portion of at least one of the lower side straps located towards the rear strap comprises a hinging arm, the hinging arm extending laterally of an elongate direction of the remainder of the lower side strap, wherein the headgear comprises a pivotable connection between the hinging arm and the rear strap or top strap.

In some configurations, the headgear is operable between the first configuration and second configuration by a hinging of the hinging arm at the pivotable connection.

In some configurations, in the first configuration the headgear is configured for securing the interface to the head of a user and in the second condition the headgear is configured for donning or doffing by a user.

In some configurations, the lower side strap is of a fixed length.

According to another aspect, the present disclosure may broadly provide a headgear for an interface, comprising:

a top strap configured to extend across a top of the user's head in use, a rear strap configured to extend across a back of the user's head in use, an upper side strap extending from an interface to the top strap, a lower side strap extending from the interface to the rear strap, the headgear being configurable into least a first configuration and a second configuration, wherein in the first configuration the lower side strap, rear strap, and interface define a first cross-sectional area, and/or a first perimeter, wherein in the second configuration the lower side strap, rear strap, and interface define a second cross-sectional area and/or a second perimeter, wherein the first cross sectional area and/or the first perimeter is less than the second cross sectional area and/or the second perimeter.

According to another aspect, the present disclosure may broadly provide a headgear for a respiratory mask, comprising:

a top strap configured to extend across a top of the user's head in use, a rear strap configured to extend across a back of the user's head in use, an upper side strap extending from an interface to the top strap, a lower side strap extending from the interface to the rear strap, the headgear being configurable into least a first configuration and a second configuration, wherein in the first configuration the lower side straps, rear strap and interface define a first cross-sectional area and/or a first perimeter, wherein in the second configuration the upper side straps, rear strap and interface define a second cross-sectional area and/or a second perimeter, wherein the first cross sectional area and/or a first perimeter is less than the second cross sectional area and/or a second perimeter.

In some configurations, in the second configuration an opening for the head of a user to the headgear is defined by the second cross sectional area.

In some configurations, the first configuration is a use configuration and the second configuration is a donning and doffing configuration In some configurations, the headgear is configurable between the first configuration and the second configuration by hinging of each lower side strap about a pivotable connection.

In some configurations, the first cross-sectional area and/or a first perimeter are measured from a bottom perspective of the headgear.

In some configurations, the second cross-sectional area and/or a second perimeter are measured from a bottom perspective of the headgear.

According to another aspect, the present disclosure may broadly provide a headgear for a respiratory mask, comprising:

a top strap configured to extend across a top of the user's head in use, a rear strap configured to extend across a back of the user's head in use an upper side strap extending from an interface to the top strap, a lower side strap extending from the interface to the rear strap, the headgear being configurable into least a first configuration where the headgear is to worn by the user and a second configuration where the headgear is to be fitted to, or removed from, a user, wherein in the first configuration the lower side strap is located inward from the upper side strap, wherein in the second configuration the lower side strap is located outward from the upper side strap.

In some configurations, the first configuration is a use configuration and the second configuration is a donning and doffing configuration In some configurations, the headgear is configurable between the first configuration and the second configuration by hinging of each lower side strap about a pivotable connection.

According to another aspect, the present disclosure may broadly provide a headgear for an interface, comprising:

a first strap, the first strap comprising:

a pair of upper side strap portions a rear strap portion a second strap, the second strap comprising:

a lower side strap portion, a top strap portion, wherein the first strap and second strap are connected at at least one connection location.

In some configurations, the first strap is configured to overlap the second strap at the at least one connection location.

In some configurations, the second strap is configured to overlap the first strap at the at least one connection location.

In some configurations, the headgear comprises a third strap, the third strap comprising:
a lower side strap portion,
a top strap portion.

In some configurations, the first strap and third strap are connected at at least one connection location.

In some configurations, the first strap is configured to overlap the third strap at the at least one connection location.

In some configurations, the third strap is configured to overlap the first strap at the at least one connection location.

In some configurations, the second strap and third strap are integrally formed as a single strap.

In some configurations, the top strap portion of the second strap and the top strap portion of the third strap are adjustably connected.

In some configurations, the first strap and second strap are continuous to a location rear of the connection location.

In some configurations, the first strap and/or third strap are continuous to a location rear of the connection location.

In some configurations, the at least one connection location is located behind a user's ear in use.

In some configurations, the first strap is continuous.

In some configurations, the first strap is a single strap.

In some configurations, the upper side strap portion(s) of the first strap is configured to connect with the interface.

In some configurations, the lower side strap portion(s) of the second strap is configured to connect with the interface.

In some configurations, the first strap comprises a first strap sleeve and a first strap core.

In some configurations, the first strap core is located within the first strap sleeve.

In some configurations, the first strap core extends through the rear strap portion of the first strap.

In some configurations, the first strap core extends through the rear strap portion of the first strap and to each of the pair of upper side strap portions.

In some configurations, the first strap core extends to the upper side strap portions to a location forward of the user's ear in use.

In some configurations, the first strap core extends to the upper side strap portions, to a location where the first strap core is aligned with a headgear connector on the interface to which the first strap connects.

In some configurations, the second strap comprise a second strap sleeve and second strap core.

In some configurations, the second strap core is located within the second strap sleeve.

In some configurations, the second strap core extends through the top strap portion of the second strap.

In some configurations, the second strap core extends through the top strap portion to the lower side strap portion.

In some configurations, the second strap core extends to the top strap portions, or to the lower side strap portions to a location forward of the user's ear in use.

In some configurations, the second strap core extends to the lower side strap portions to a location where the second strap core is aligned with a headgear connector on the interface to which the second strap connects.

In some configurations, the third strap comprises a third strap sleeve and third strap core.

In some configurations, the third strap core is located within the third strap sleeve.

In some configurations, the third strap core extends through the top strap portion of the third strap.

In some configurations, the third strap core extends through the top strap portion of the third strap and to the lower side strap portion.

In some configurations, the third strap core extends to the lower side strap portion to a location forward of the user's ear in use.

In some configurations, the third strap core extends to the lower side strap portion to a location where the third strap core is aligned with a headgear connector on the interface to which the third strap connects.

In some configurations, the first strap core and/or the second strap core and/or the third strap core is rigid or semi-rigid.

In some configurations, the first strap sleeve and/or the second and/or the third strap sleeve strap sleeve is a textile or fabric.

In some configurations, the first strap sleeve and/or the second strap sleeve and/or the third strap sleeve is more extensible in a direction along the length of the first strap and/or second strap and/or the third strap, than along the width of the first strap and/or second strap and/or the third strap.

In some configurations, the first strap sleeve and/or the second strap sleeve and/or the third strap sleeve is continuous along the length of the first strap and/or second strap and/or the third strap.

In some configurations, the first strap sleeve and/or the second strap sleeve and/or the third strap sleeve is uninterrupted along the length of the first strap and/or second strap and/or the third strap.

In some configurations, the first strap sleeve and/or the second strap sleeve and/or the third strap sleeve is connected to the first strap core and/or the second strap core and/or the third strap core at the connection location.

In some configurations, the first strap sleeve and/or the second strap sleeve and/or the third strap sleeve is able to move relative to the first strap core and/or the second strap core and/or the third strap core.

In some configurations, a rear loop is formed by the rear strap portion of the first strap, the top strap portion of the second strap and the top strap portion of the third strap.

In some configurations, the top strap portion configured to extend across a top of the user's head in use.

In some configurations, the rear strap portion configured to extend across a back of the user's head in use In some configurations, the lower side strap portion(s) of the second strap and/or the third strap connect to interface.

In some configurations, the upper side strap portion(s), of the first strap connect to interface.

According to another aspect, the present disclosure may broadly provide a headgear for an interface, comprising:
a first strap, the first strap comprising:
a pair of upper side strap portions,
a rear strap portion,
a second strap, the second strap comprising:
a pair of lower side strap portions,
a top strap portion,
wherein the first strap and second strap are connected at at least one connection location.

In some configurations, the rear strap portion is located between the pair of upper side strap portions.

In some configurations, the top strap portion is located between the pair of lower side strap portions.

In some configurations, the second strap is continuous.

In some configurations, the second strap is a single strap.

In some configurations, the second strap comprises an adjustment mechanism.

In some configurations, the adjustment mechanism is located in the top strap portion, or central portion of the second strap.

In some configurations, the headgear comprises a pair of connection locations.

In some configurations, the at least one connection location is located behind a user's ear in use.

In some configurations, the first strap is configured to overlap the second strap at the at least one connection location.

In some configurations, the second strap is configured to overlap the first strap at the at least one connection location.

In some configurations, the first strap is continuous.

In some configurations, the first strap is a single strap.

In some configurations, the upper side strap portions of the first strap is configured to connect with the interface.

In some configurations, the lower side strap portions of the second strap is configured to connect with the interface.

In some configurations, the first strap comprises a first strap sleeve and first strap core.

In some configurations, the first strap core is located within the first strap sleeve.

In some configurations, the first strap core extends through the rear strap portion or the central portion of the first strap.

In some configurations, the first strap core extends through the central portion of the first strap and to each of the pair of upper side strap portions.

In some configurations, the first strap core extends to the upper side strap portions to a location forward of the user's ear in use.

In some configurations, the first strap core extends to the upper side strap portions, to a location where the first strap core is aligned with a connection location on the interface to which the first strap connects.

In some configurations, the second strap comprise a second strap sleeve and second strap core.

In some configurations, the second strap core is located within the second strap sleeve.

In some configurations, the second strap core extends through the top strap portion or the central portion of the second strap.

In some configurations, the second strap core extends through the top strap portion and to each of the pair of end portions or wherein the second strap core extends through the central portion of the second strap and to each of the pair of lower side strap portions.

In some configurations, the second strap core extends to each of the pair of end portions, or to the lower side strap portions to a location forward of the user's ear in use.

In some configurations, the second strap core extends to each of the pair of end portions, or to the lower side strap portions, to a location where the second strap core is aligned with a connection location on the interface to which the second strap connects.

In some configurations, the first strap core and/or the second strap core is rigid or semi-rigid.

In some configurations, the first strap sleeve and/or the second strap sleeve is a textile or fabric.

In some configurations, the first strap sleeve and/or the second strap sleeve is more extensible in a direction along the length of the first strap and/or second strap, than along the width of the first strap and/or second strap.

In some configurations, the first strap sleeve and/or the second strap sleeve is continuous along the length of the first strap and/or second strap.

In some configurations, the first strap sleeve and/or the second strap sleeve is uninterrupted along the length of the first strap and/or second strap.

In some configurations, the first strap sleeve and/or the second strap sleeve is connected to the first strap core and/or the second strap core at the connection location.

In some configurations, a rear loop is formed by the rear strap portion of the first strap and the top strap portion of the second strap.

In some configurations, the top strap configured to extend across a top of the user's head in use.

In some configurations, the rear strap configured to extend across a back of the user's head in use In some configurations, the lower side strap portions, or the end portions of the second strap connect to interface.

In some configurations, upper side strap portions, or the end portions of the first strap connect to interface.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

Embodiments described herein can also be said broadly to relate to the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

DETAILED DESCRIPTION

Figure 1:
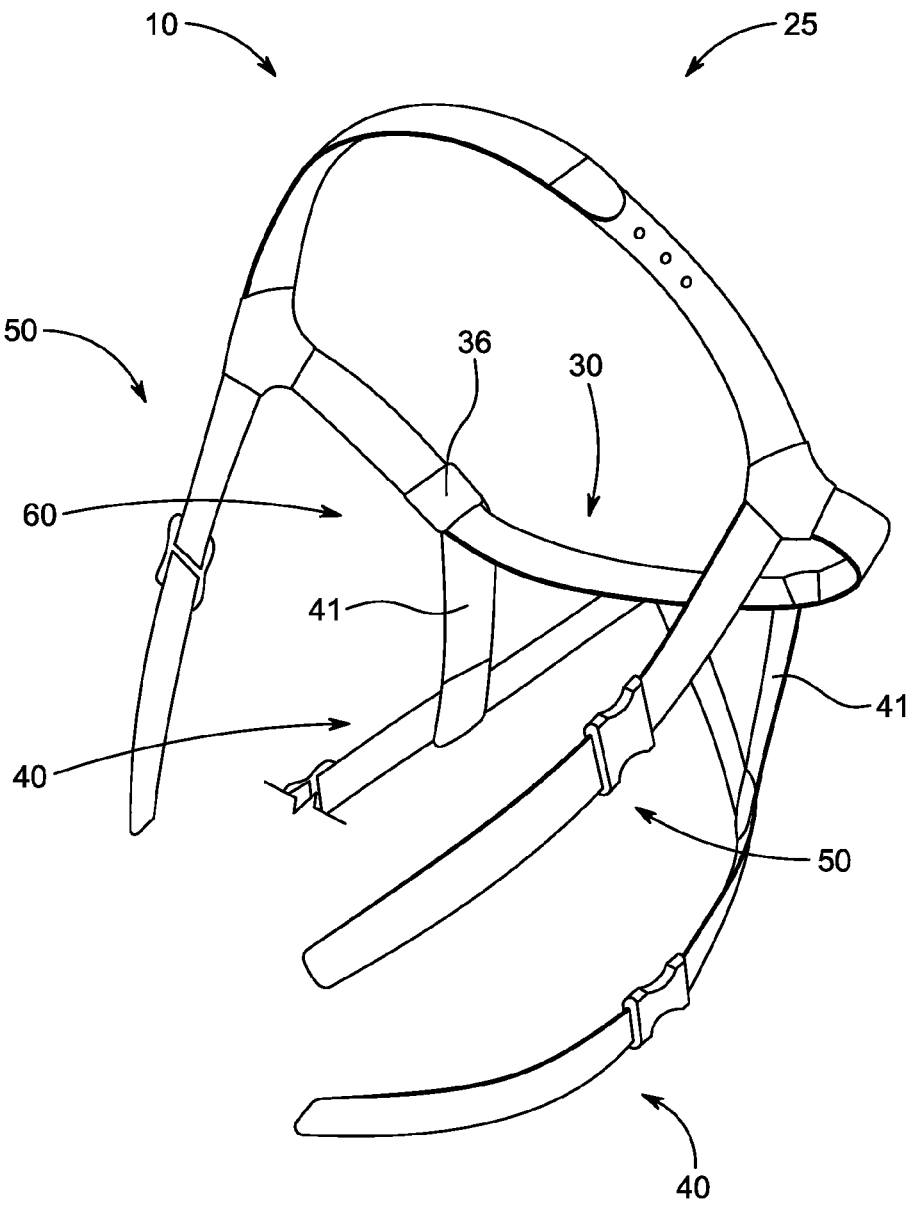
FIG. 1 shows a view of a headgear.

Disclosed is a headgear comprising one or more pivotable connections 60. The pivotable connection 60 allows the headgear to move between a donning and doffing configuration where the user can easily don and doff the headgear to an in use configuration where the user can wear the headgear.

In the donning and doffing configuration the lower side strap(s) 40 are moved laterally outward by the pivotable connection 60 to increase the area available for a user to put on or remove the headgear. Once the user has donned the headgear 10 the lower side strap(s) 40 are moved laterally inward to the in use configuration.

On removal of the headgear 10, the lower side strap(s) 40 are again moved laterally outward by the pivotable connection 60 to the donning and doffing configuration to increase the area available for a user to put on or remove the headgear.

The different headgear configurations provided by the pivotable connection 60 allow for donning and doffing of the headgear without having to disconnect any straps from the interface 1 or adjust the length of any of the headgear straps.

Because adjustment and/or disconnection of straps is potentially reduced when donning and doffing, straps of the headgear for example the upper side straps 50 and lower side straps 40 can be made of inextensible materials (as opposed to extensible materials which may otherwise be required to be included to allow for ease of fitting). Inextensible materials (as opposed to extensible materials) may allow for a more consistent application of force to the interface 1, and as a consequence provide for a better seal between the interface 1 and a user's face.

In embodiments which have a pair of pivotable connections 60 the lateral movement of both lower side straps 40, this further increases the area available for a user to don or doff.

FIGS. 1 to 4 show a headgear 10 for an interface 1.

The headgear 10 comprises a rear loop 20. The rear loop 20 extends around the rear of the user's head in use.

The rear loop 20 comprises a top strap 25 and a rear strap 30. The top strap 25 is configured to extend across a top of the user's head in use. The rear strap 30 is configured to extend across a back of the user's head in use.

The top strap 25 and/or the rear strap 30 may be made of a rigid material, or a semi-rigid material or a non-rigid material or any combination of rigid, semi-rigid and non-rigid materials. In some embodiments the top strap 25 and/or the rear strap 30 may be inextensible.

Figure 2:
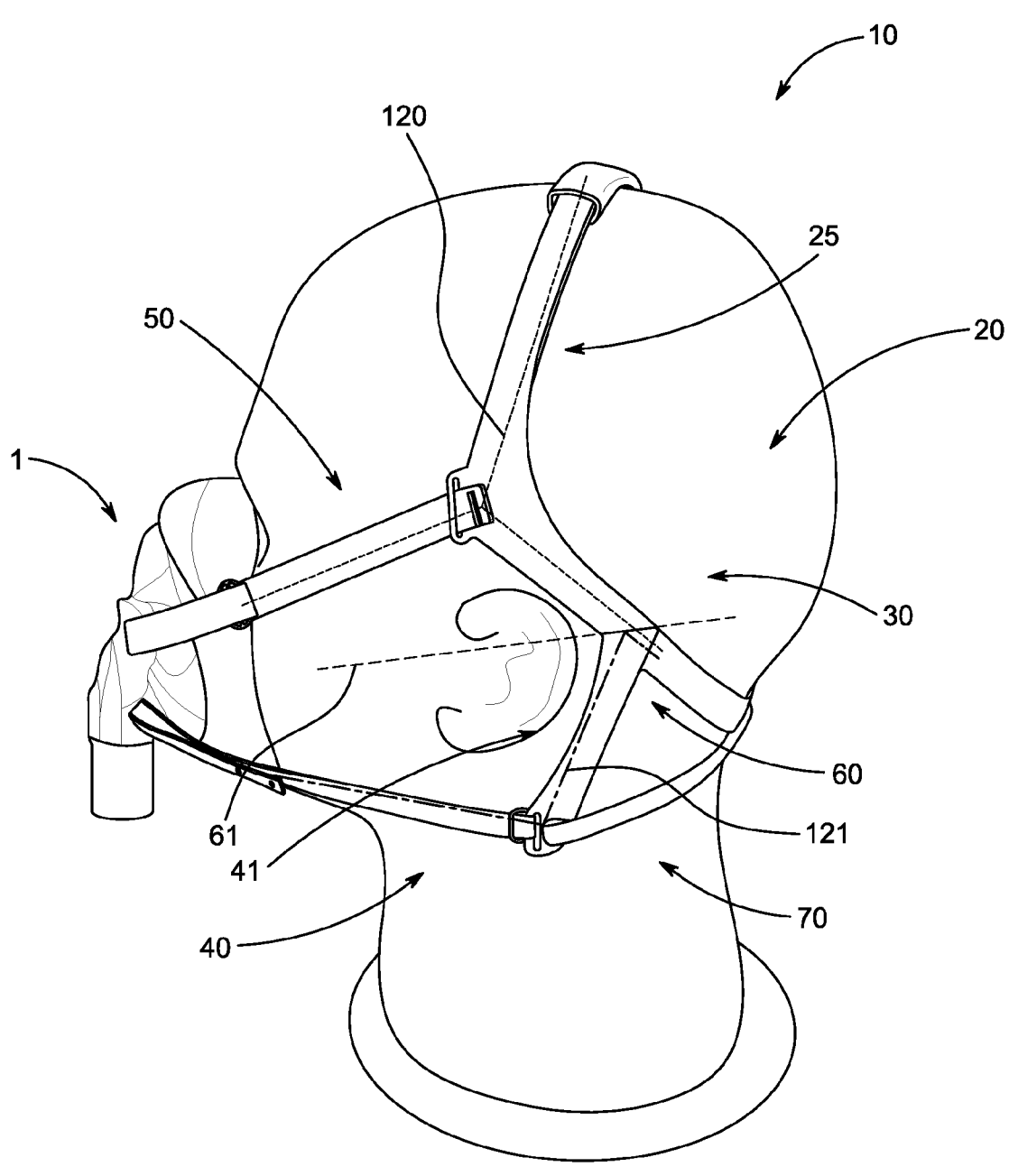
FIG. 2 shows a side view of a headgear and interface.

The top strap 25 and rear strap 30 are connected to each other to form the rear loop 20. The top strap 25 and rear strap 30 may be connected at a location above each ear while in use (for example as shown in FIG. 2).

The top strap 25 is connected at an angle relative to the rear strap 30. In some embodiments the top strap 25 is connected to the rear strap 30 at an angle of about 90 degrees to about 180 degrees, or about 110 degrees to about 160 degrees.

The top strap 25 is connected to the rear strap 30 at a location above a user's ear.

The top strap 25 and rear strap 30 may be integrally formed, for example as a single piece rear loop.

As illustrated by FIG. 2, the rear strap 30 may comprise a rear portion 35 and a pair of front portions 31. The front portions 31 are located on each side of the rear portion 35. The front portion 31 is configured to connect with each side of the top strap 25.

The rear portion 35 is configured to be located behind a user's head in use.

The front portions 31 may be made of a different material than the rear portion 35.

The rear portion 35 of the rear strap 30 may be semi-rigid or non-rigid. In some embodiments the rear portion 35 of the rear strap 30 is inextensible.

The front portion 31 of the rear strap 30 may be rigid. In some embodiments the front portions 31 of the rear strap 30 is inextensible.

The front portions 31 may be configured to connect with the top strap 25 as described above.

The top strap 25 may be located forward of a midline of a user's head. In some embodiments, the top strap 25 may be located rear of a midline of a user's head. In some embodiments, the top strap 25 may be located in line a midline of a user's head As shown for example in FIG. 1 the length of the rear loop 20 may be configurable. The rear loop 20 may comprise one or more adjustment features 26. The adjustment features 26 allow for the length of the rear loop 20 to be varied. Varying the length of the rear loop 20 may improve fitting of the headgear 10 to a patient.

Figure 3:
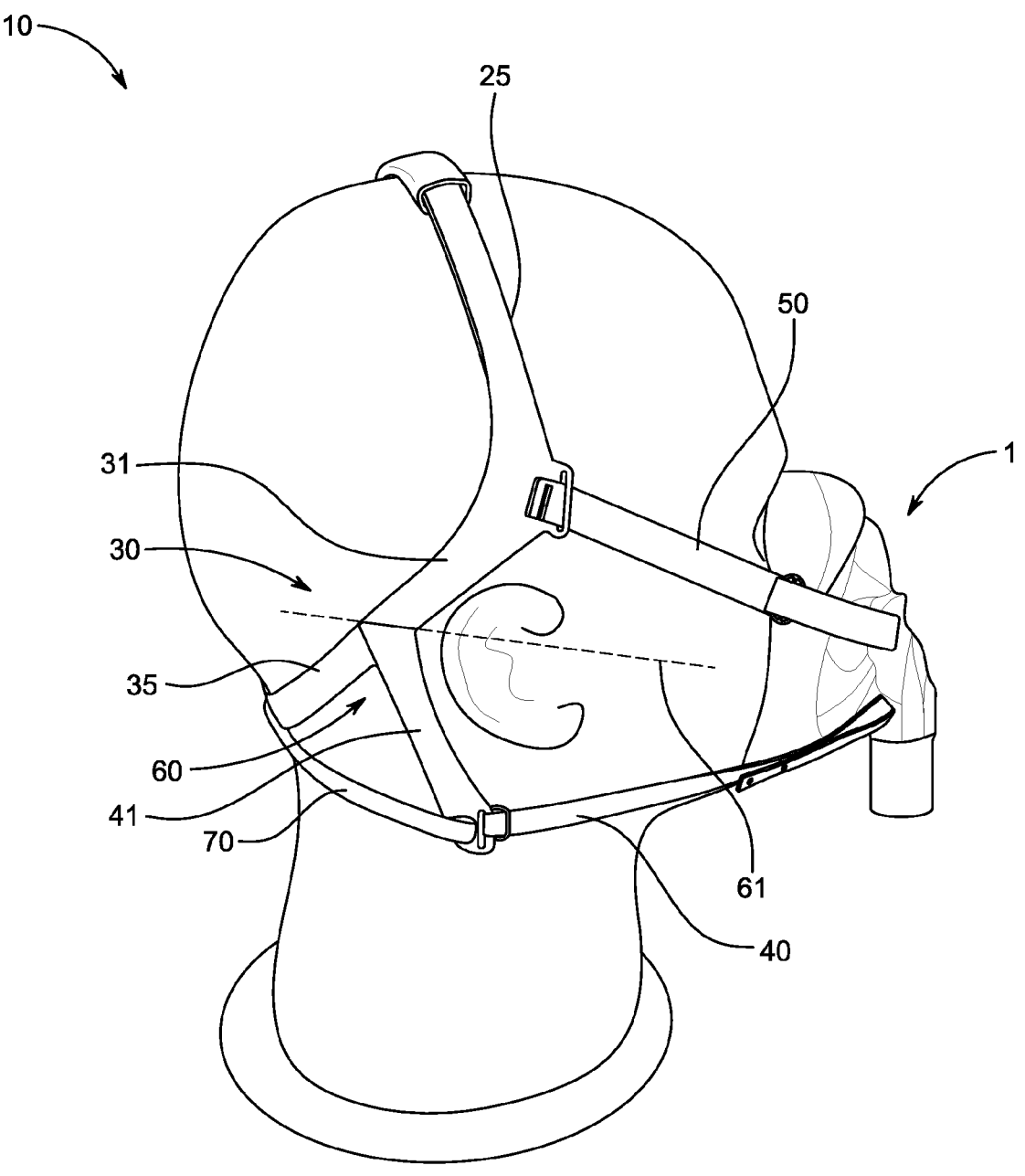
FIG. 3 shows a side view of a headgear and interface.

As shown for example in FIGS. 1 and 3, the adjustment features 26 are provided as part of the top strap 25. The adjustment feature(s) 26 may be provided as part of the rear strap 30, or both the top strap 25 and the rear strap 30.

The adjustment features 26 allow for the adjustment of the length of the top strap 25 and/or the rear strap 30.

Figure 4:
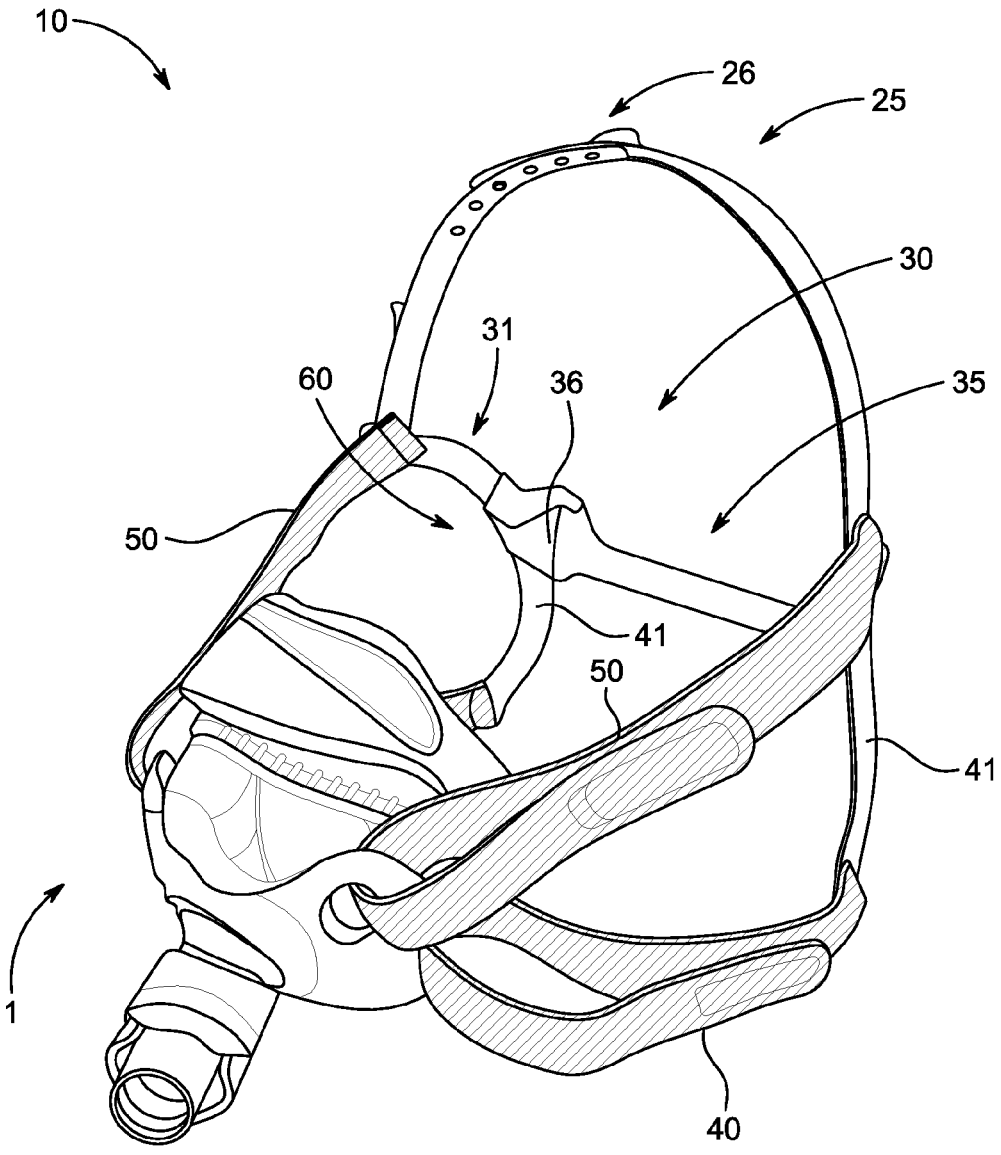
FIG. 4 shows a front perspective view of a headgear and interface.

As shown for example in FIGS. 1 and 4 the adjustment features comprise one or more studs and corresponding holes.

The adjustment features 26 may comprise one or more hook and loop material.

The adjustment features 26 may comprise one or more clips.

The headgear 10 comprises a lower side strap 40. The lower side strap 40 extends from the rear loop 20 to an interface 1. The lower side strap 40 may extend from the top strap 25 and/or the rear strap 30 of the rear loop 20.

The headgear 10 comprises an upper side strap 50. The upper side strap 50 extends from the rear loop 20 to an interface 1. The upper side strap 50 may extend from the top strap 25 and/or the rear strap 30 of the rear loop 20. The upper side strap 50 may extend from the rear loop 20 at a location where the top strap 25 and rear strap 30 are connected.

In some embodiments, the top strap 25 and/or the rear strap 30 may comprise adjustment features.

The headgear 10 comprises a pair of upper side straps 50 and a pair of lower side straps 40, each upper and lower side strap pair being located on each side of the headgear 10.

The upper side straps 50 and lower side straps 40 are non-rigid. In some embodiments, the upper side straps 50 and lower side straps 40 may be non-rigid, semi-rigid, rigid or any combination of these.

In some embodiments, the headgear 10 may comprise a two-loop configuration. In the two-loop configuration, the headgear 10 is separated into two separate loops.

Figure 15:
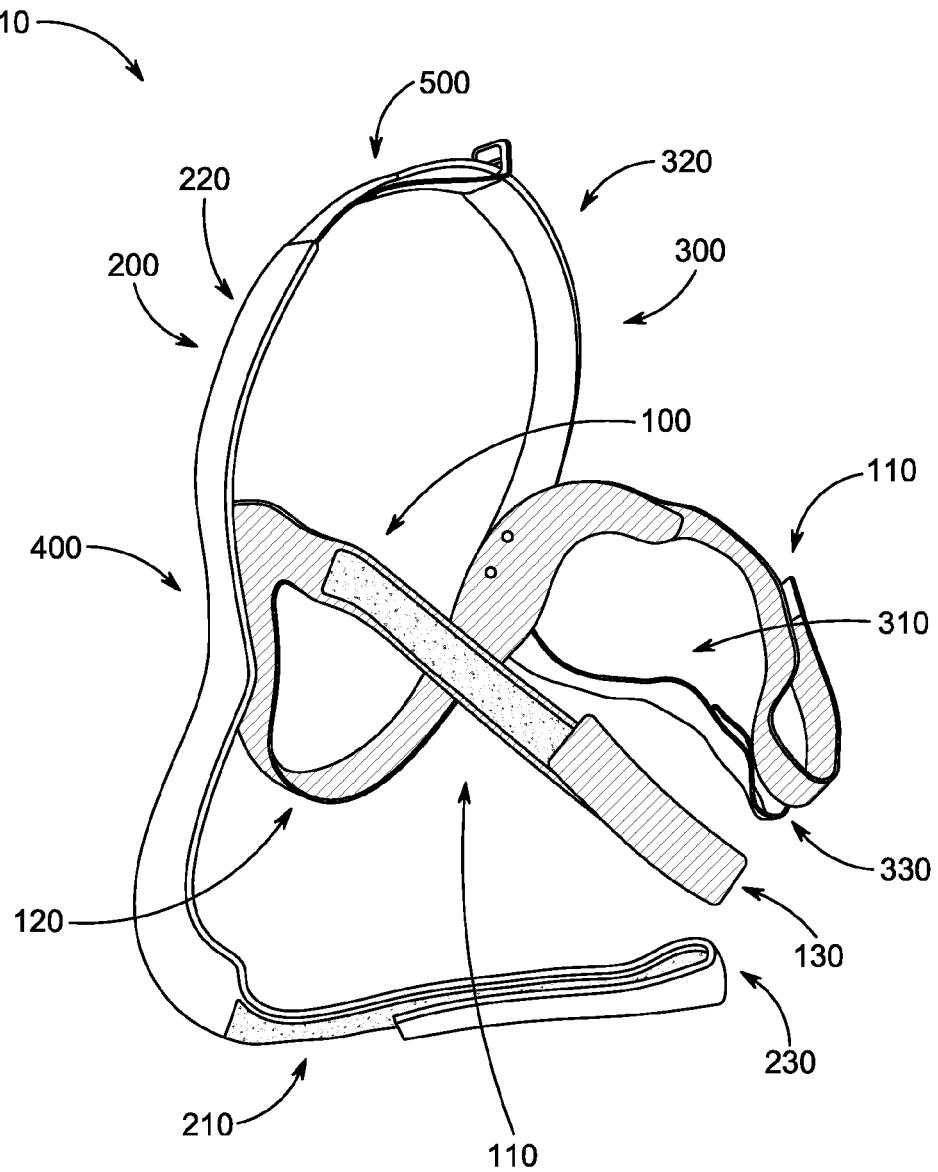
FIG. 15 shows a headgear.

As shown for example by FIG. 15 the two loops are connected or assembled at one or more connection locations.

Figure 14:
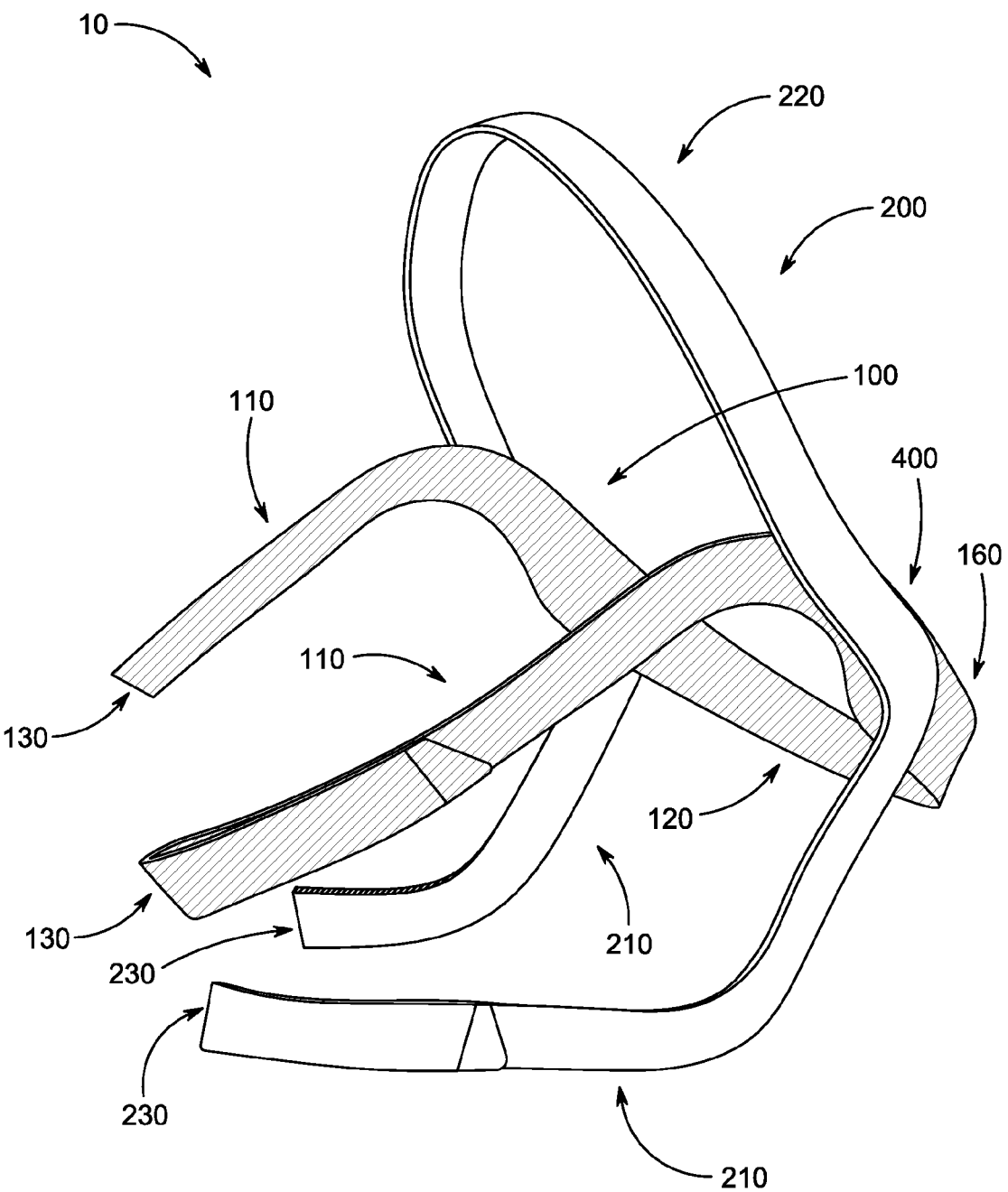
FIG. 14 shows a headgear.

In some embodiments, as shown for example in FIG. 14, the headgear 10 comprises a first strap 100 and a second strap 200.

The first loop comprises a first strap and the second loop may comprise a second strap.

The first strap 100 comprises a pair of upper side strap portions 110 and a rear strap portion 120.

The first strap 100 comprises a pair of end portions (for example upper side strap portions 110) and a central portion (for example rear strap portion 120).

In some embodiments, it will be appreciated the first strap 100 may be divided into separate straps, for example two separate straps (for example in the manner as described below with relation to the second strap 200, and the third strap 300.)

The second strap 200 comprises a pair lower side strap portion 210, a top strap portion 220.

A rear loop is formed by the rear strap portion 120 of the first strap 100 and the top strap portion 220 of the second strap 200.

In some embodiments, for example as shown in 15 the headgear 1 comprises a first strap and second strap and a third strap.

It will be appreciated that any embodiments which describe having a third strap 300, may also be configured in a two strap configuration (for example by forming the second strap 200 and third strap 300 as a second strap 200.)

Figure 21:
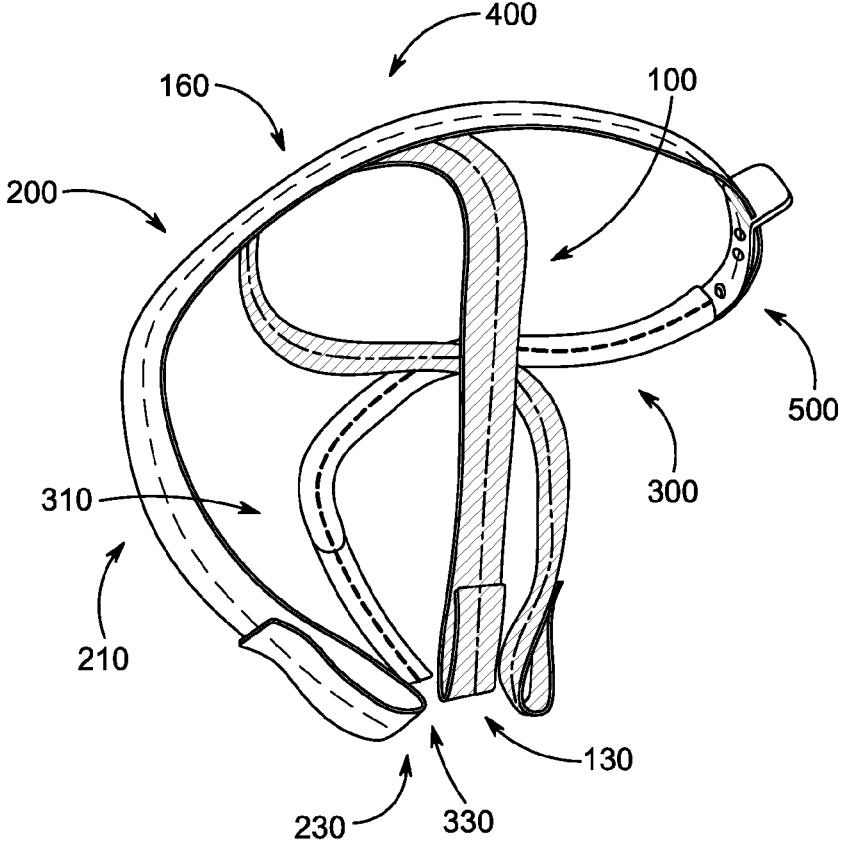
FIG. 21 shows a headgear.

For example FIG. 21 shows a headgear with a second strap 200 and a third strap 300, however this headgear could be configured so that the second strap 200 and third strap 300 is formed as the second strap 200.

In embodiments with a third strap 300, the first loop comprises a first strap and the second loop may comprise a second strap and a third strap.

The third strap 300 comprises a lower side strap portion 310, and a top strap portion 320.

In embodiments with a third strap 300 a rear loop is formed by the rear strap portion 120 of the first strap 100, the top strap portion 220 of the second strap 200 and the top strap portion 320 of the third strap 300.

In embodiments with a third strap 300, the second strap 200 comprises a lower side strap portion 210, a top strap portion 220.

The lower side strap portion(s) 210, 310 of the second strap 200 and/or the third strap 300 connect to interface 1.

The upper side strap portion(s) 110 of the first strap 100 connect to interface 1.

It will be appreciated that when discussing features of the second strap 200 below these features could equally be applied to the third strap 300.

In some embodiments, the second strap and/or third strap comprise one or more pivotable connections described elsewhere in the specification.

In embodiments comprising a pivotable connection, part of the lower side strap portion(s) 210, 310 may form the hinging arm.

As shown for example in FIG. 15, the first strap 100 and second strap 200 are connected at at least one connection location 400.

Also shown for example in FIG. 15, the first strap 100 and third strap 300 are connected at at least one connection location 400.

In some embodiments, the connection location 400 may be located in a region adjacent to a user's ear. For example, the connection location may be located above and/or behind a user's ear.

Figure 16:
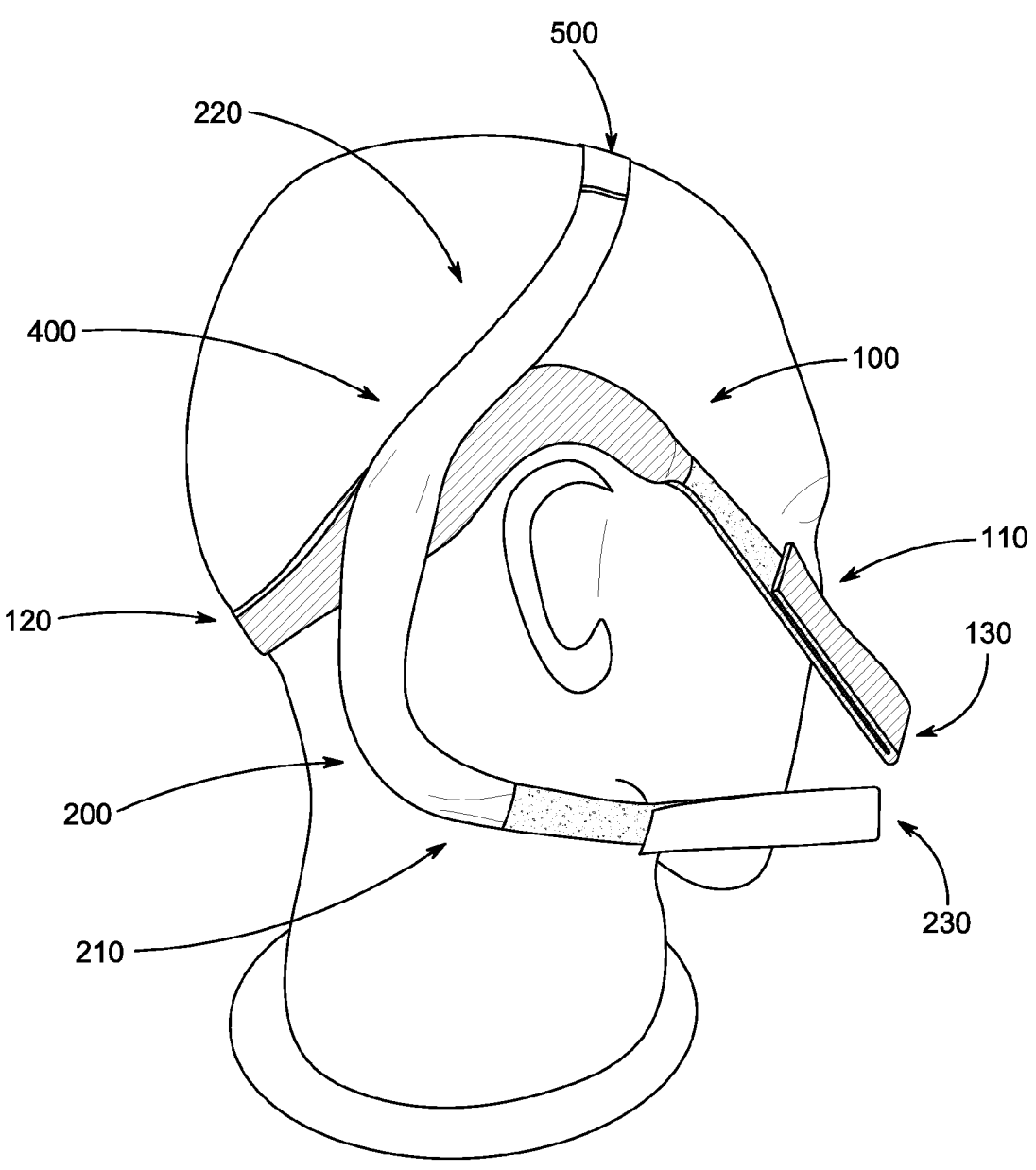
FIG. 16 shows a side view of a headgear in use.

As shown for example in FIG. 16, the connection location 400 is located behind a user's ear in use.

In some embodiments, the connection location 400 may be located within the height of a user's ear.

In embodiments having a pivotable connection, the connection location may be located above the pivotable connection. Optionally, to allow the hinging arm to lift away from the first strap.

The first strap 100 may be configured to overlap the second strap 200 at the at least one connection location 400. Alternatively and as shown in FIG. 16, the second strap 200 is configured to overlap the first strap 100 at the at connection location 400. In this configuration, the second strap 200 lies on the outside of the first strap 100.

In embodiments with a third strap, the first strap 100 may be configured to overlap the third strap 300 at the at least one connection location 400. Alternatively, the third strap 300 may be configured to overlap the first strap 100 at the at least one connection location 400.

In some embodiments, the at least one connection location 400 of the first strap 100 may be located between the top strap portion 220 and each upper side strap portion 110.

In some embodiments, the at least one connection location 400 of the second strap 200 may be located between the top strap portion lower side strap portion(s) 210.

In some embodiments, with a third strap 300, the at least one connection location 400 of the third strap 300 may be located between the top strap portion lower side strap portion 310.

Figure 19:
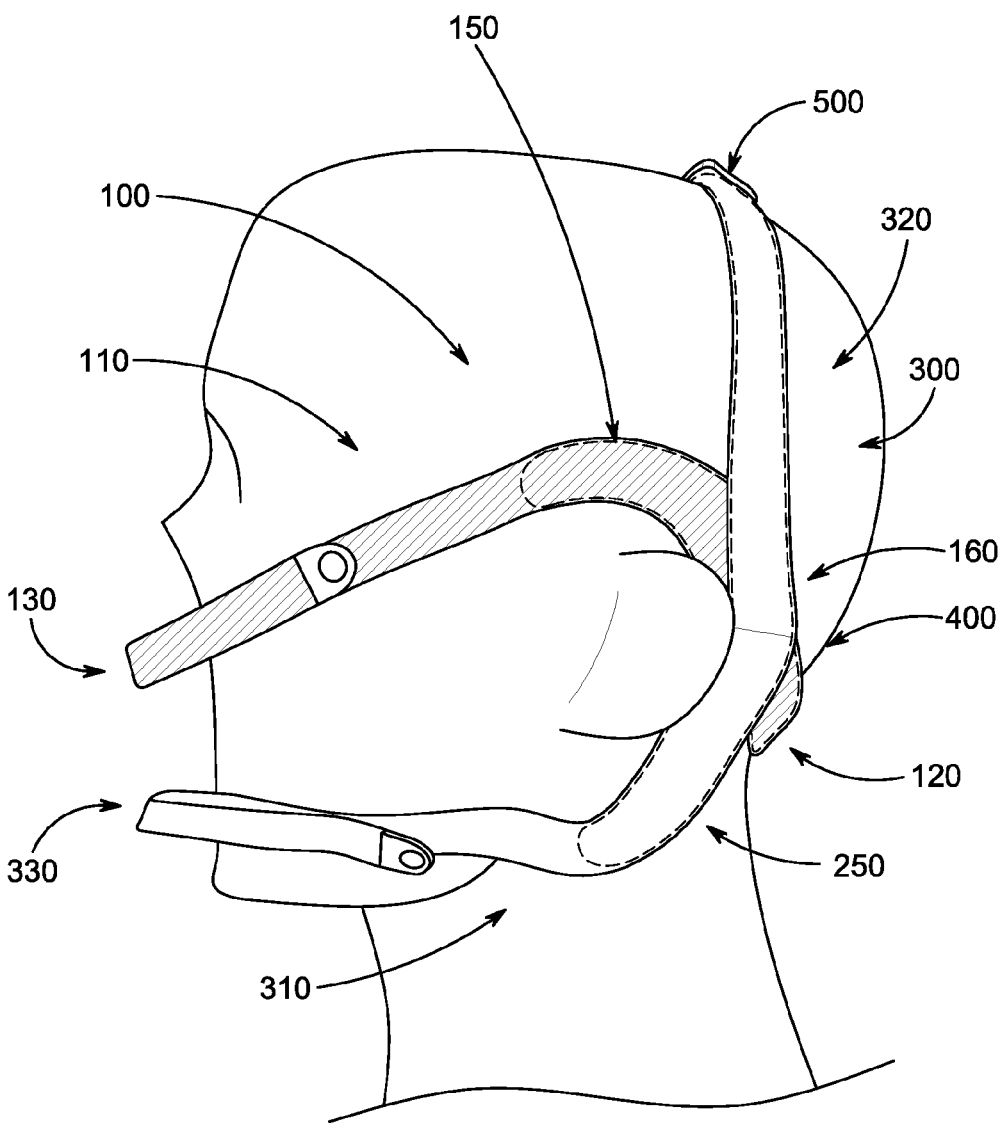
FIG. 19 shows a side view of a headgear in use.

As shown for example in FIG. 19, the start of the top strap portion 320 of the third strap 300 overlaps the start of the rear strap portion 120 of the first strap 100 with the connection location 400 being approximately middle of the overlapping region 160.

The first strap 100 may be configured to overlap the second strap 200 and/or the third strap 300 in an overlapping region 160.

The overlapping region 160 may extend along a portion of the first strap 100 and the second strap 200 and/or the third strap 300.

The connection location 400 may be located in the overlapping region 160.

In some embodiments in the overlapping region of the first strap 100 may be parallel to the second strap 200 and/or the third strap 300.

As described above, the connection location 400 may be located where the first strap 100 overlaps the second strap 200 and/or where the first trap 100 overlaps the third strap 300. Alternatively, the connection location 400 may comprise one more or locations where the second strap 200 and/or third strap 300 overlap(s) the first strap 100.

In some embodiments, the straps may be connected at the connection location 400 along the entire overlapping region or only part of the overlapping region.

Figure 22:
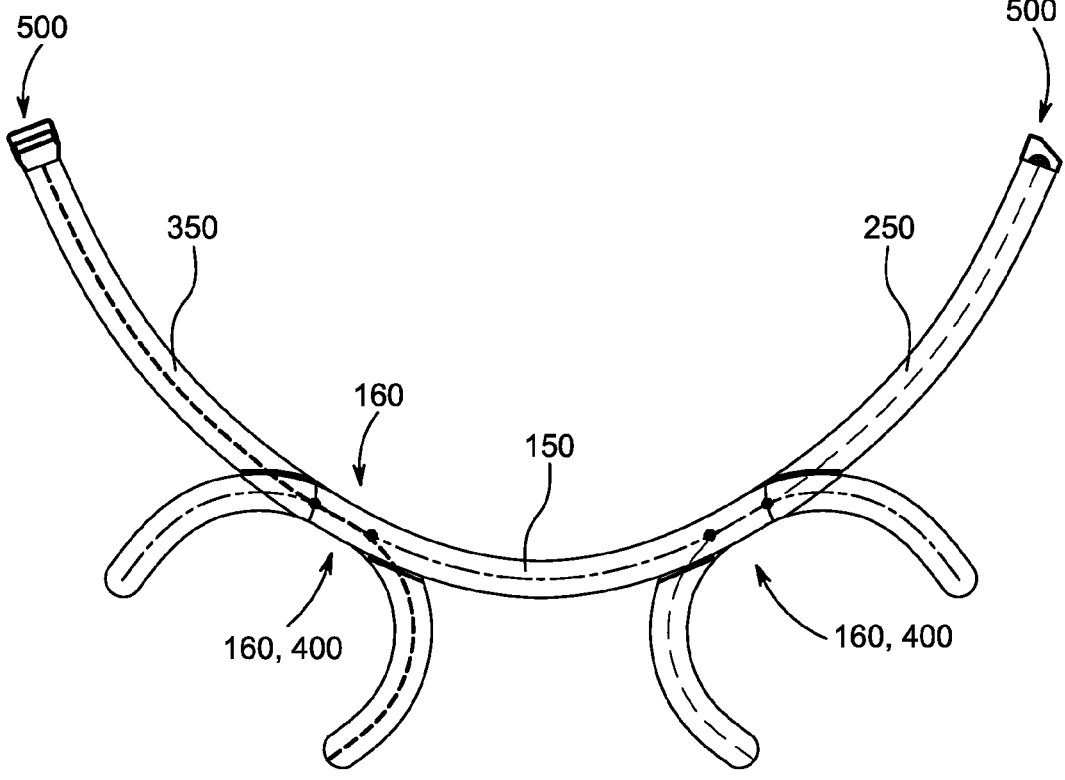
FIG. 22 shows strap cores.

The first strap 100 and second strap 200 and/or third strap 300 may be connected at the connection location 400 by; stitching, connection features (for example pins as shown in FIG. 22) radio frequency (RF) welding, gluing or any other suitable welding or joining methods.

As shown in FIG. 14, the second strap 200 and the third strap 300 are integrally formed as a single strap 200. Alternatively and as shown for example in FIG. 15, the second strap 200 and the third strap 300 are formed as separate straps.

In some embodiments, the top strap portion 220 of the second strap 200 and top strap portion 320 of the third strap 300 may be provided with one or more adjustment features 500.

In some embodiments, the adjustment feature 500 may be used to change the length of the top strap portions of the second and third straps.

Figure 20:
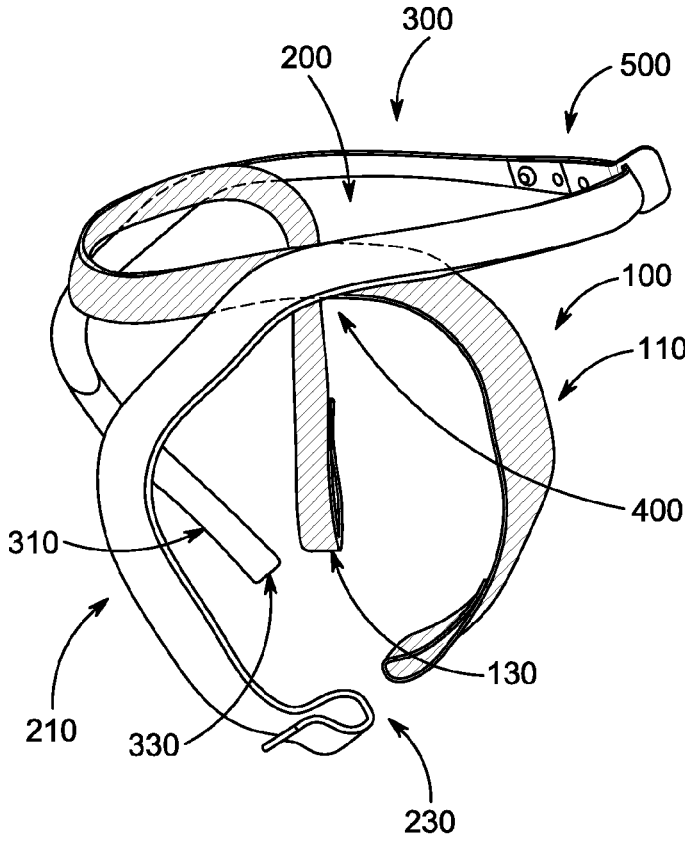
FIG. 20 shows a headgear.

As shown for example in FIGS. 20 and 21, the top strap portion 220 of the second strap 200 and the top strap portion 320 of the third strap 300 are adjustably connected via adjustment feature 500 comprising studs and corresponding holes.

In some embodiments, the adjustment feature 500 may comprise any suitable means for adjusting the lengths of the second and third straps 200,300, such as but not limited to clips or hook and loop fasteners.

As shown for example in FIG. 14, the first strap 100 and second strap 200 are continuous.

In some embodiments, the first strap 100 may comprise one or more adjustment features 500.

In some embodiments, the first strap 100 and second strap 200 are continuous to a location rear of the connection location 400, optionally from where the first strap 100 and second strap 200 connect to the interface 1.

As shown for example in FIG. 15, in embodiments with a third strap 300, the first strap 100 and third strap 300 are continuous.

In some embodiments, the first strap 100 and third strap 300 are continuous to a location rear of the connection location 400, optionally from where the first strap 100 and third strap 300 connect to the interface 1.

The first strap 100 and/or the second strap 200 and/or the third strap 300 may be a single strap.

The upper side strap portions 110 of the first strap 100 are configured to connect with the interface 1.

In some embodiments, each upper side strap portion 110 may include an interface connector portion 130 for connecting to the first strap to interface 1.

In some embodiments, the interface connector portion 130 allows for the adjustment of the length of the upper side strap 120. As shown for example in FIGS. 20 and 21, the interface connector portion 130 comprises a hook and loop material.

The interface connector portion 130 may be connected to a corresponding headgear connector on the interface 1.

For example, the headgear connector may comprise a slot on the interface for receiving the interface connector portion 130.

Figure 17:
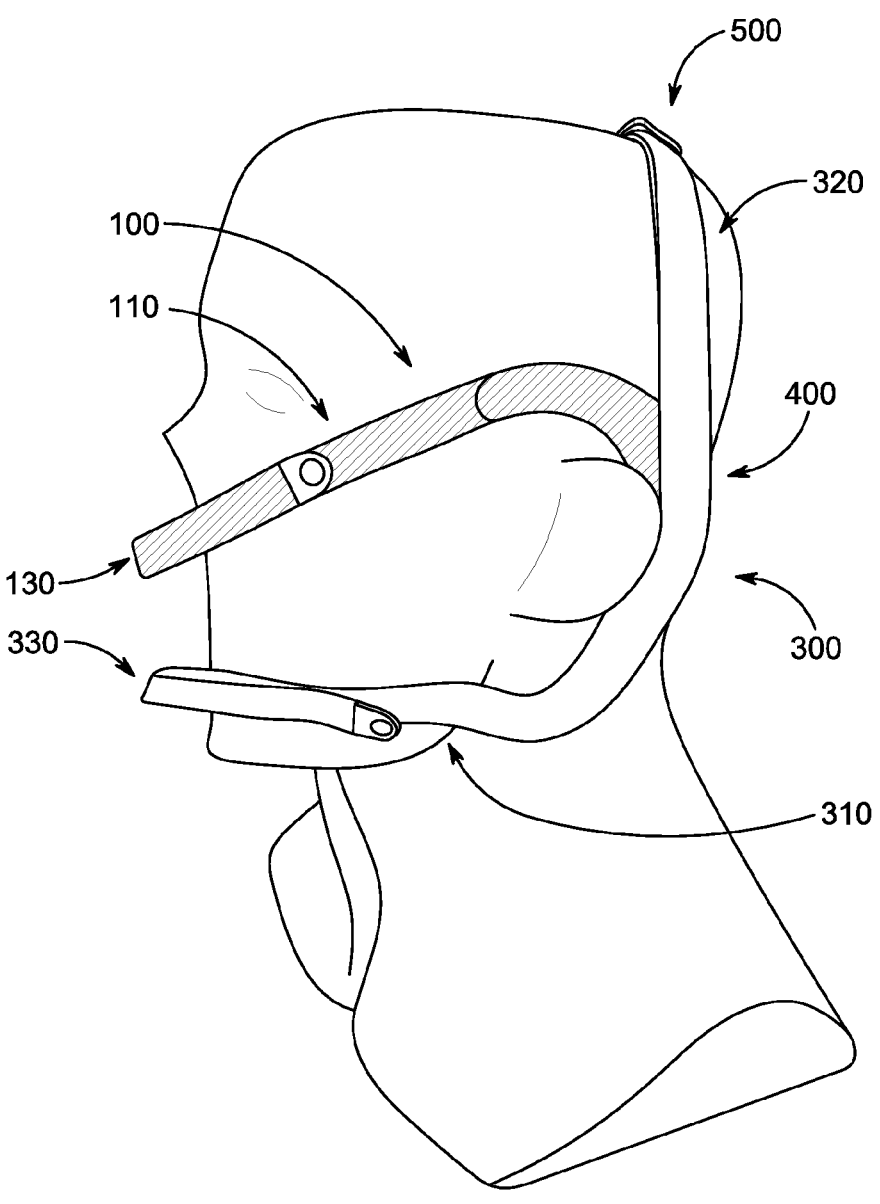
FIG. 17 shows a rear view of a headgear in use.
Figure 18:
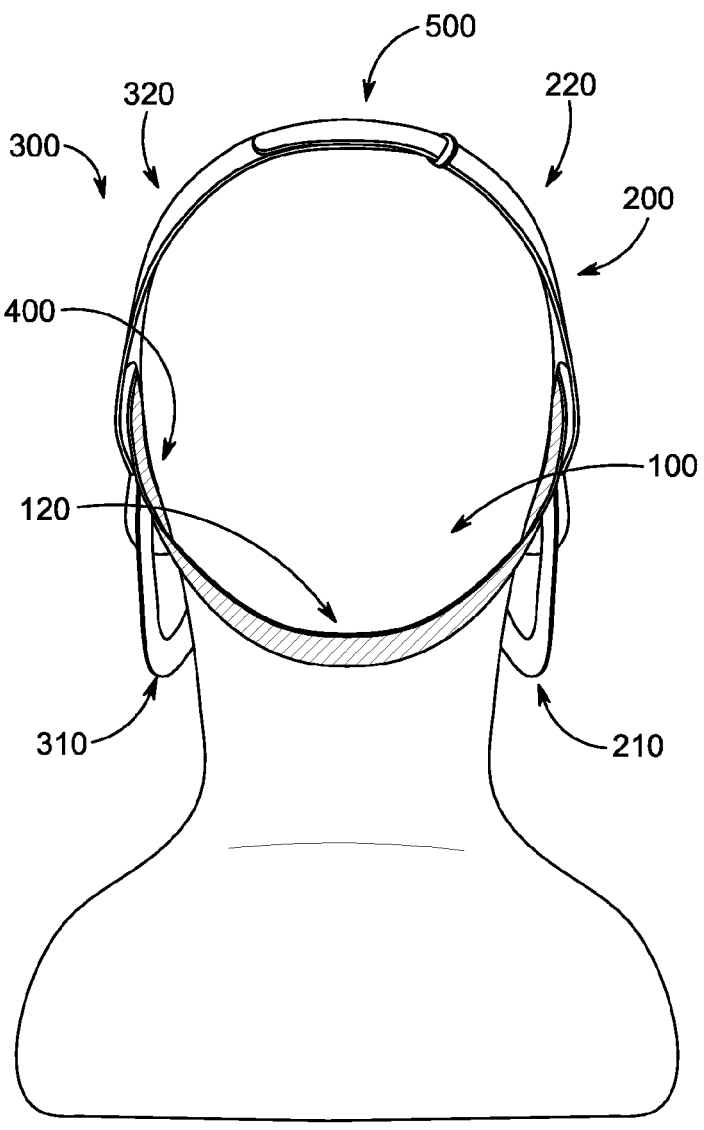
FIG. 18 shows a side view of a headgear in use.

In some embodiments, the interface connector portion 130 may comprise one or more of clips. As shown for example in FIG. 17, the free end of interface connector portion 130 may comprise a gripping feature.

The lower side strap portion(s) 210 of the second strap 200 is configured to connect with the interface 1.

The lower side strap portions 210 and lower side strap portions 310 may each comprise interface connector portions 230, 330 similar to the first strap.

The straps of headgear 10 may each comprise one or more strap sleeves and one or more strap cores.

The first strap 100 comprises a first strap sleeve 140 and a first strap core 150.

The second strap 200 comprises a second strap sleeve 240 and a second strap core 250.

In embodiments which comprise a third strap 300, the third strap comprises a third strap sleeve 340 and a third strap core 350.

Figure 25:
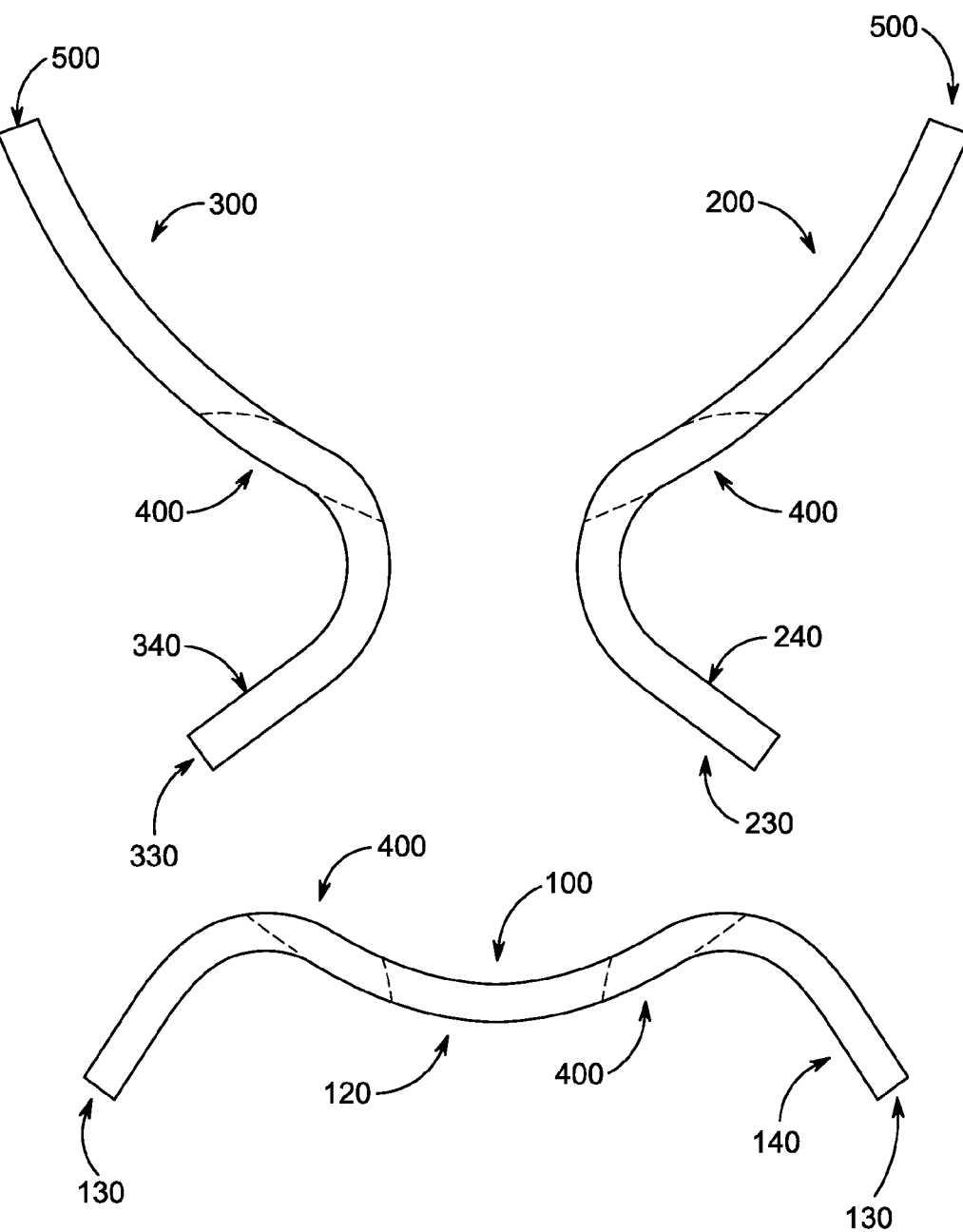
FIG. 25 shows strap sleeves for the first, second and third straps without corresponding strap cores.
Figure 25A:
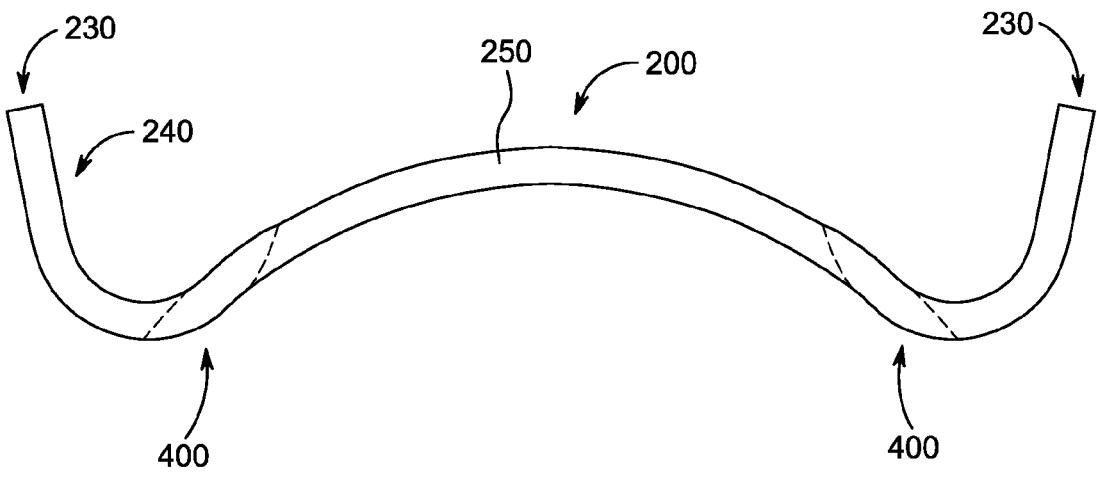
FIG. 25A shows strap sleeves for the first and second straps without corresponding strap cores.
Figure 25A:
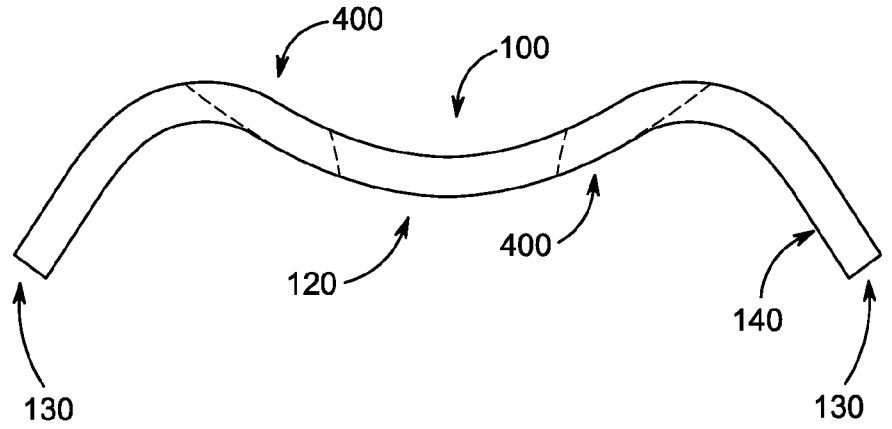

In some embodiments, the headgear 10 may comprise one or more strap sleeves without any strap cores (for example as shown in FIGS. 25 and 25A).

In this description where reference is made to a strap, strap sleeve, or strap core it will be appreciated this could apply to any one or combination of the first strap 100 and/or the second strap 200 and/or the third strap 300

Figure 24:
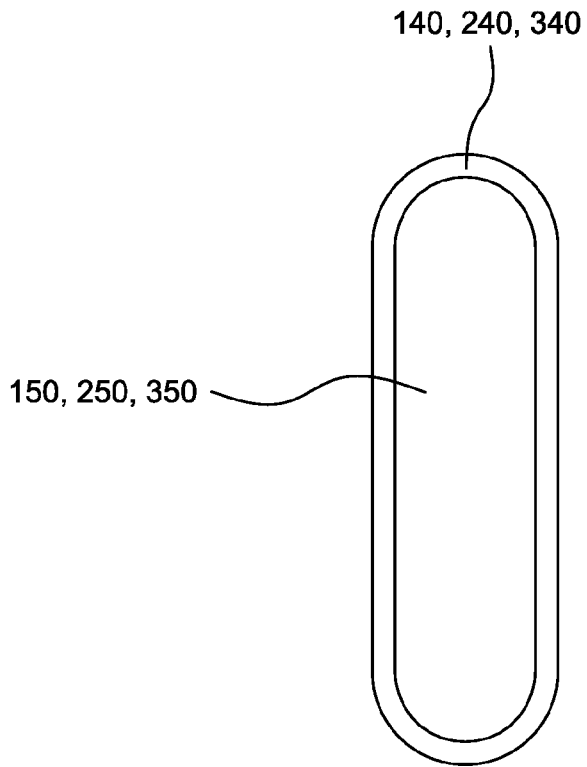
FIG. 24 shows a cross section of a strap having a strap sleeve and a strap core.

FIG. 24 shows a cross section of a strap sleeve 140, 240, 340 with a strap core 150, 250, 350.

The strap sleeve 140, 240, 340 may have a tubular structure with opening in the centre for accommodating the strap core 150, 250, 350.

The strap sleeve 140, 240, 340 may be formed around or fitted over the strap core. The strap core 150, 250, 350 may be retained within the strap sleeve 140, 240, 340 by welding or other means of attaching the strap sleeve 140, 240, 330 to the strap core 150, 250, 350.

As shown for example in FIGS. 14 to 21, each strap sleeve is continuous.

In some embodiments, the first strap sleeve 140 is continuous along the length of the first strap 100.

In some embodiments, the second strap sleeve 240 is continuous along the length of the second strap 200.

In some embodiments, the third strap sleeve 240 is continuous along the length of the third strap 200.

The strap sleeve(s) 140, 240, 340 can be made of a fabric or textile.

In some embodiments the fabric may be a woven fabric.

In some embodiments, the fabric may be flexible so as to conform to the shape and curvatures of the headgear straps.

The strap sleeve(s) 140, 240, 340 may be more extensible in a direction along the length of the strap 100, 200, 300, than along the width of the strap 100, 200, 300.

In some embodiments, the strap sleeve 140, 240, 340 may also comprise different elasticity in different directions of the strap sleeve. For example, the strap sleeve 140, 240, 340 may be elastic (or relatively more elastic) in a transverse (weft) direction but inelastic (or relatively less elastic) in a longitudinal (warp) direction. Alternatively, the strap sleeve may be semi-elastic in the longitudinal direction to allow for movement of the interface on the face of a user.

The strap sleeve 140, 240, 340 may comprise the same material or a combination of different materials.

In some embodiments, the interior (user contacting) surface of the straps 100, 200, 300 may comprise a softer fabric while the exterior (non-user contacting) surface of the straps may comprise a harder (more durable) fabric material. The softer fabric on the interior surface may increase the comfort of a user while the harder exterior fabric may improve the durability of the headgear.

In some embodiments, as shown for example in FIG. 21, the exterior surface of the upper side strap portions 110 may comprise hook and loop material for attaching the strap 100 to a headgear connector on the interface.

In some embodiments, the fabric or textile material of each strap sleeve may be provided with different colours to allow differentiation of the upper and lower side strap portions and improve usability of the headgear.

The strap core 150, 250, 350 may extend the full length or part of the strap sleeve.

The strap 100, 200, 300 may comprise one or more strap cores 150, 250, 350. For example, the strap 100, 200, 300 may comprise a single strap core 150, 250, 350 extending the full length or part of the strap.

In some embodiments, the strap sleeve may comprise two or more strap cores 150, 250, 350.

In some embodiments, the strap sleeve may comprise no strap cores.

In some embodiments, the first strap 100 may comprise a strap core 150 in each of the upper side strap portions 110 and second strap core 150 in the rear strap portion 120.

In some embodiments, the strap core 250, 350 in the lower side strap 210, 310 portion(s) may extend further forward than the strap core 150 in the upper side strap portion 110.

The strap core can be made of rigid or semi-rigid material.

In some embodiments, the strap core 150, 250, 350 comprises a flexible plastic material.

In some embodiments, the strap core 150, 250, 350 may be made of a nylon based polymer.

In some embodiments, the strap core 150, 250, 350 may comprise a constant thickness along the length of the strap core 150, 250, 350.

In some embodiments, the strap core 150, 250, 350 may comprise variable thickness along the length of the strap core 150, 250, 350.

Variable thickness in the strap core 150, 250, 350 may provide variable levels of rigidity or flexibility at different parts of the strap core 150, 250, 350.

In some embodiments, the strap core 150, 250, 350 in the lower side strap portion and/or the upper side strap portion may be stiffer at a region below the user's ear and/or the overlapping region than at a location forward of a user's ear.

In some embodiments, the strap core 150, 250, 350 may be stiffer in the top strap portion or the rear strap portion than the lower side strap portion or the upper side strap portion.

In some embodiments the strap core 150, 250, 350 may be about 0.7 mm in thickness in the top strap portion or the rear strap portion.

In some embodiments the strap core 150, 250, 350 may be about 0.3 mm to about 0.5 mm in thickness in the lower side strap portion or the upper side strap portion.

In some embodiments, a strap core in the lower side strap portion may be stiffer at a region below the user's ear but reduce in stiffness towards the interface 1.

In some embodiments, a strap core 150, 250, 350 in the lower side strap portion may be thicker at a region below the user's ear and/or the overlap region than at a location forward of a user's ear.

In some embodiments, a strap core in the lower side strap portion may be thicker at a region below the user's ear but reduce in thickness towards the interface 1.

The reduction in thickness (and stiffness) of the lower side strap portion may allow the strap to more easily conform to the cheek region. This may reduce the pressure applied to the sensitive cheek region, particularly when the user is sleeping or lying on their side.

In some embodiments, the headgear 10 may comprise zones with variable rigidity. For example, the headgear zone forward of a user's ear may be non-rigid (without strap cores), while the headgear zone behind the patient's ear may be semi-rigid (comprising one or more semi-rigid strap cores). The transition between semi-rigid and non-rigid zone may be flush or seamless to avoid causing irritation or discomfort to a user.

The strap core 150, 250, 350 is rigid or semi-rigid.

The strap sleeve 140, 240, 340 is continuous along the length of the strap 100, 200, 300.

The strap sleeve 140, 240, 340 is uninterrupted along the length of the strap 100, 200, 300.

The strap sleeve 140, 240, 340 is connected to the strap core 150, 250, 350 at the connection location 400 and/or the overlap region.

The strap sleeve 140, 240, 340 may be able to move relative to the strap core 150, 250, 350.

As shown in FIG. 19, the first strap 100 comprises a first strap sleeve 140 and a first strap core 150 (denoted by a dashed line). The first strap core 150 is located within the first strap sleeve 140.

The first strap core 150 may extend through the rear strap portion 120 of the first strap 100.

The first strap core 150 may extend through the rear strap portion 120 of the first strap 100 and to each of the pair of upper side strap portions 110.

The first strap core 150 may extend to the upper side strap portions 110 to a location forward of the user's ear in use.

The first strap core 150 may extend to the upper side strap portions 110 to a location where the first strap core 150 is aligned with a headgear connector or a connection location on the interface to which the first strap 100 connects.

The second strap 200 may comprise a second strap sleeve 240 and a second strap core 250 (denoted by a dashed line).

The second strap core 250 may be located within the second strap sleeve 240.

The second strap core 250 may extend through the top strap portion 220 of the second strap 200.

The second strap core 250 may extend through the top strap portion 220 to the lower side strap portion 210.

The second strap core 250 may extend to the top strap portion 220, or to the lower side strap portion 210 to a location forward of the user's ear in use.

The second strap core 250 may extend to the lower side strap portions 210 to a location where the second strap core 250 is aligned with a headgear connector or a connection location on the interface to which the second strap connects.

The third strap 300 may comprise a third strap sleeve 340 and third strap core 350.

The third strap core 350 may be located within the third strap sleeve 340.

The third strap core 350 may extend through the top strap portion 320 of the third strap 300.

The third strap core 350 may extend through the top strap portion 320 of the third strap 300 and to the lower side strap portion 310.

The third strap core 350 may extend to the lower side strap portion 310 to a location forward of the user's ear in use.

The third strap core 350 extends to the lower side strap portion 310 to a location where the third strap core 350 is aligned with a headgear connector on the interface to which the third strap connects.

FIG. 22 shows an example of the first strap core 150, second strap core 250 and third strap core 350 with no corresponding sleeves.

Figure 22A:
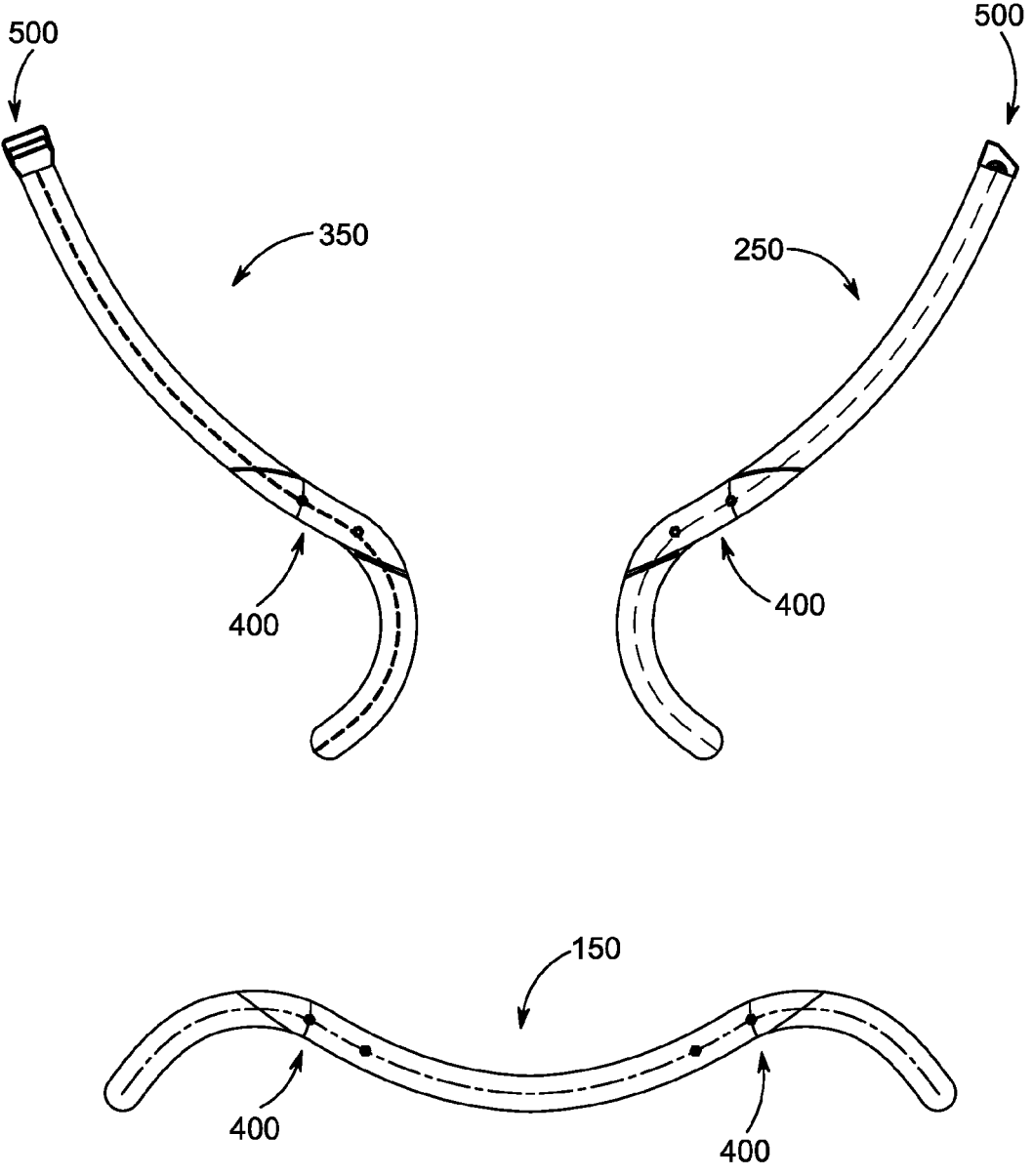
FIG. 22A shows strap cores for the first, second and third straps.

FIG. 22A shows an example of the first strap core 150, second strap core 250 and third strap core 350 with no corresponding sleeves, and where the cores 150, 250, 350 are note connected to each other and shown separately.

Figure 22B:
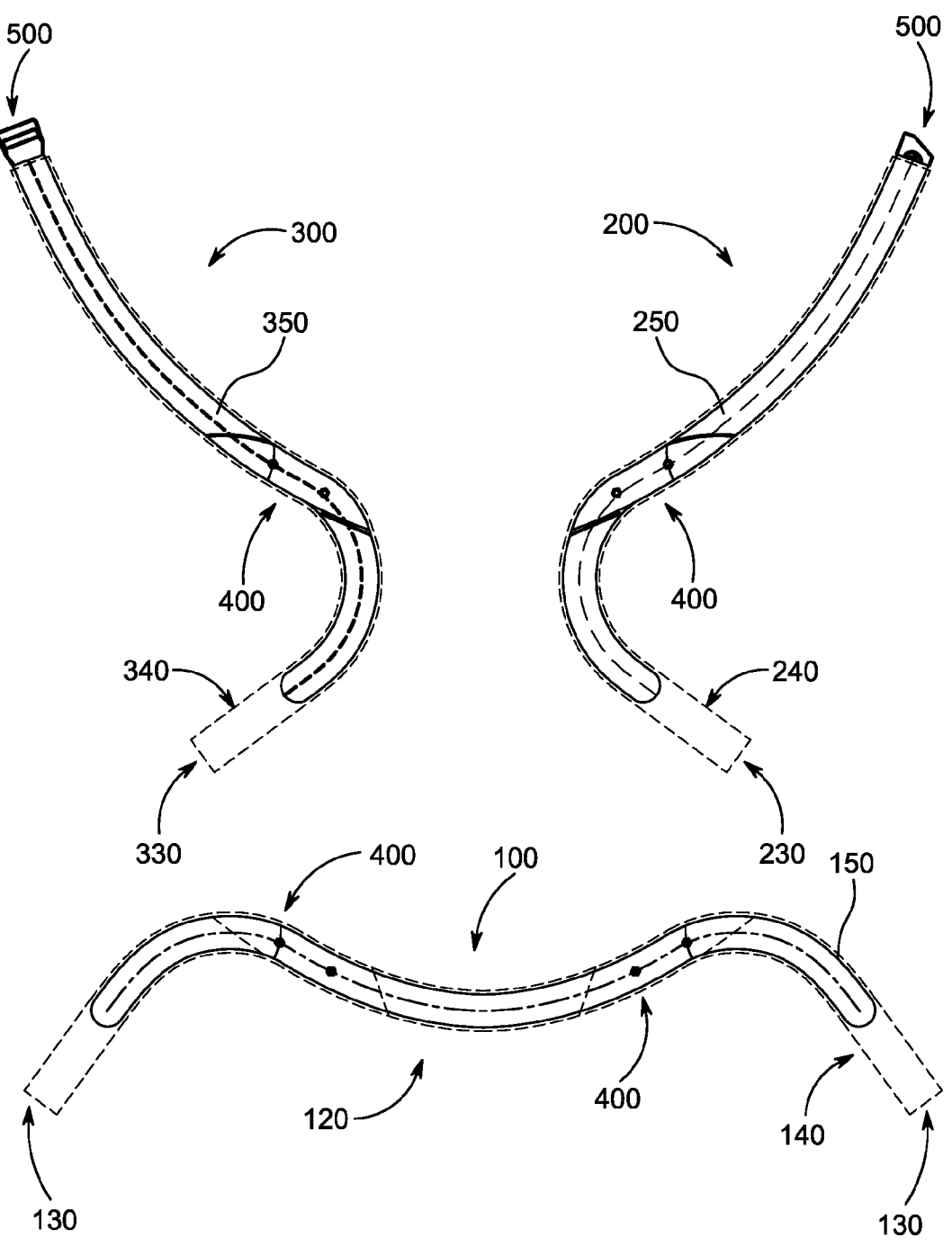
FIG. 22B strap cores for the first, second and third straps with corresponding strap sleeves.

FIG. 22B shows an example of the first strap core 150, second strap core 250 and third strap core 350 with corresponding strap sleeves 140, 240, 340.

FIG. 22B shows the strap sleeves 140, 240, 340 as extending past the end of the corresponding strap core 150, 250, 350. As discussed in more detail elsewhere in the specification.

Figure 23:
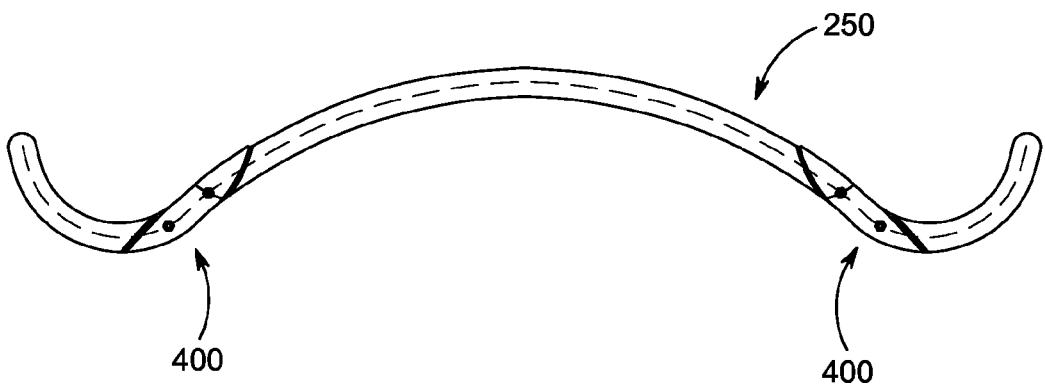
FIG. 23 shows strap cores for the first and second straps.
Figure 23:
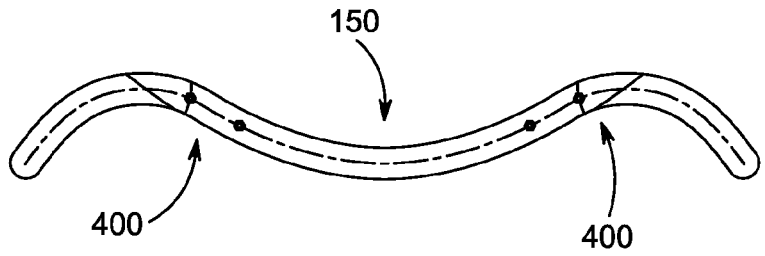

FIG. 23 shows an example of the first strap core 150 and second strap core 250 with no corresponding sleeves, and where the cores 150, 250 are not connected to each other and shown separately.

Figure 23A:
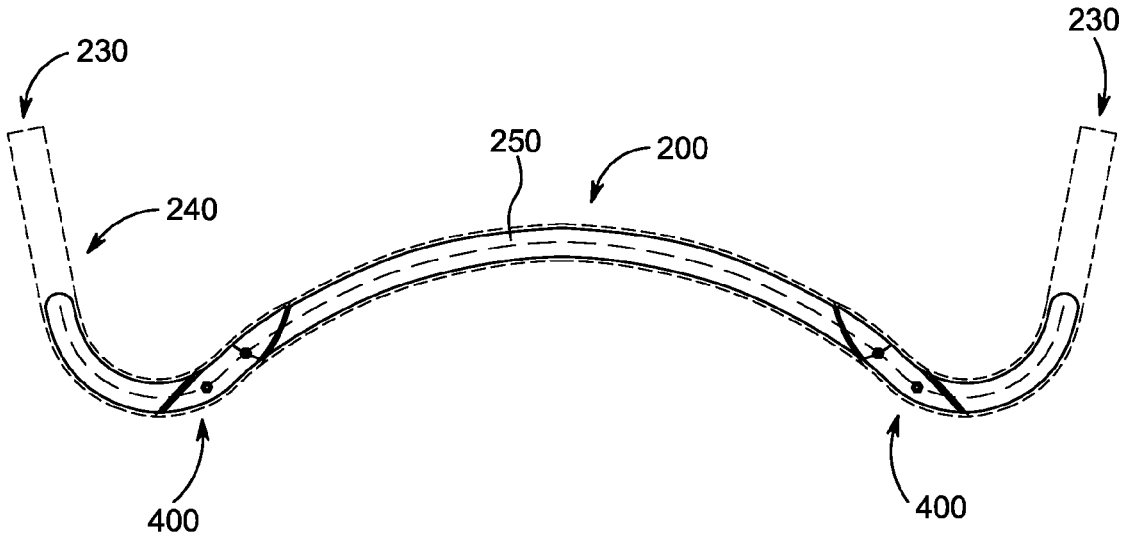
FIG. 23A strap cores for the first and second straps with corresponding strap sleeves.
Figure 23A:
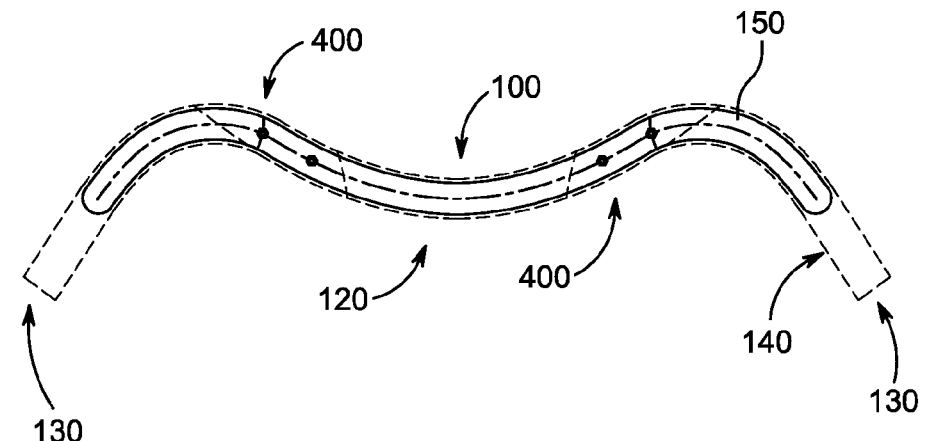

FIG. 23A shows the strap sleeves 140, 240 as extending past the end of the corresponding strap core 150, 250. As discussed in more detail elsewhere in the specification.

In some embodiments, straps 100, 200, may comprise strap sleeves 140, 240 without any strap cores.

In embodiments with a third strap, the third strap 300 may comprise a third strap sleeve 340 without any strap cores.

FIG. 25 shows an example of the straps 100, 200, 300 comprising strap sleeves 140, 240, 340 with no corresponding strap cores.

FIG. 25A shows an example of the straps 100, 200 comprising strap sleeps 140, 240 with no corresponding strap cores.

It will be appreciated that the construction as shown in FIGS. 25 and 25A may have corresponding strap cores located inside the strap sleeve.

In some embodiments the strap sleeves 140, 240, 340 may be at least in part be replaced by a strap (for example a rectangular or lie-flat strap).

In some embodiments, for example as shown in FIG. 1 and FIG. 2, the headgear 10 may comprise one or more elastic straps 70. The elastic strap 70 may apply a force to the lower side straps 40 in a direction towards the center of the headgear.

In some embodiments, the elastic strap 70 may apply a force to pull the lower side straps 40 towards each other.

In some embodiments, the elastic strap may apply a force to pull the lower side straps 40 towards each the rear portion 35 of the rear strap 25.

In some embodiments, the elastic strap 70 apply a force to the lower side straps 40 in a downward direction.

In FIG. 1 the elastic straps 70 are shown as being connected between each lower side strap 40 and the rear strap 30 of the rear loop 20. In some embodiments, a single elastic strap 70 may be connected between the lower side straps.

The elastic straps 70, are connected to a hinging arm 41, or the lower side strap 40 (described in more detail below). The elastic straps 70 may be connected an end of the hinging arm 41 located away from the pivotable connection 60.

The elastic straps 70 may provide a moment about the pivotable connection 60 (as described in more detail below).

The interface 1 may comprise a mask frame and a cushion module, the mask frame comprising a breathing gas inlet configured to receive a supply of breathable gas and to deliver the breathable gas to the cushion module, the cushion module being configured to form a seal with a user's face.

The interface 1 may be a mask interface. In some embodiments, the interface is a nasal and oral mask.

Figure 5:
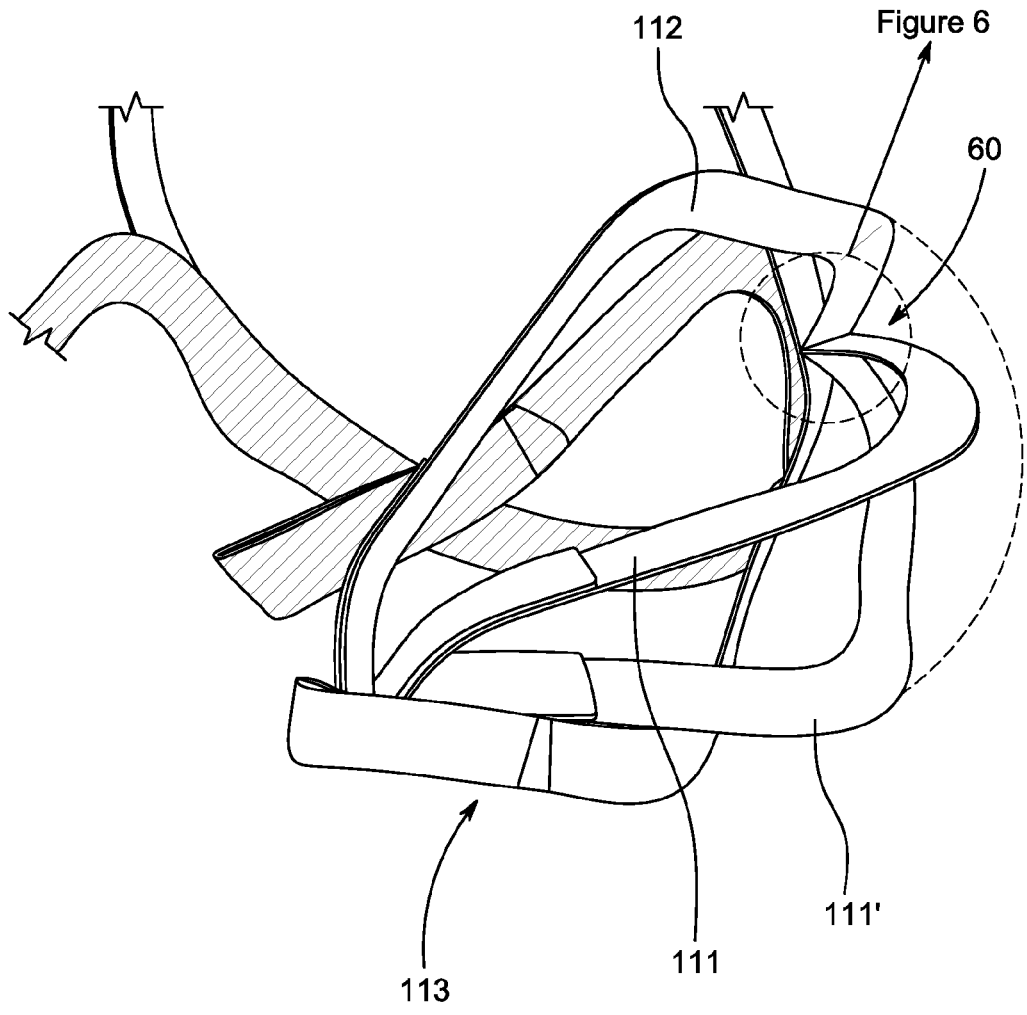
FIG. 5 shows a headgear illustrating different states of a lower side strap.

As shown for example in FIGS. 2 and 5, the headgear 10 comprises one or more pivotable connections 60.

The headgear 10 comprises a pair of pivotable connections 60. Each pivotable connection 60 is located between the upper side strap 50 and lower side strap 40 of each upper and lower side strap pair, or is on the each lower side strap 40.

It will be appreciated that a pivotable connection 60 may be provided on a single side, or both sides of the headgear 10.

As shown for example in FIGS. 1 to 3, the pivotable connection 60 is located between the lower side strap 40 and the rear loop 20. Alternatively, in some embodiments, the pivotable connection 60 may be located on the lower side strap 40.

Figure 4A:
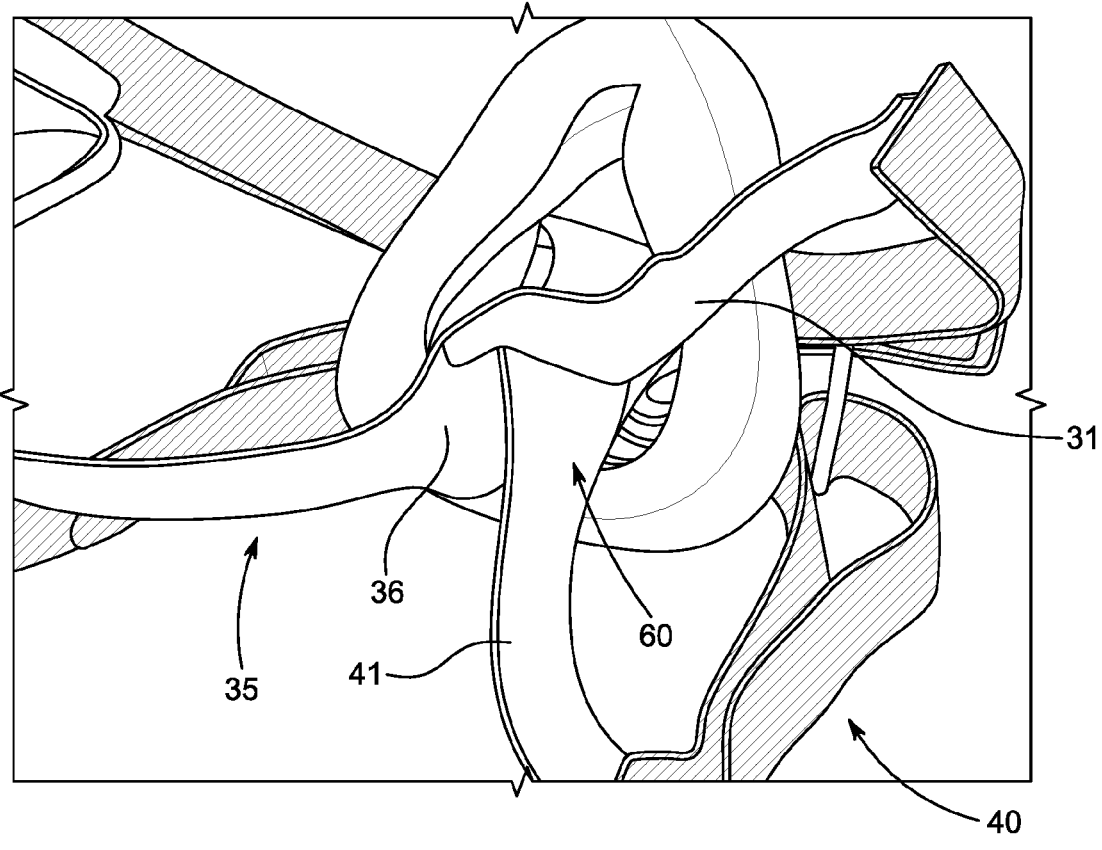
FIG. 4A shows a pivotable connection of a headgear.

As illustrated by for example FIG. 4A the pivotable connection 60 is located at a connection point between the lower side strap 40 and the rear strap 30.

The pivotable connection 60 is configured to allow for lateral movement of the lower side strap 40 (for example as shown in FIG. 5).

As illustrated by FIG. 5, the pivotable connection 60 is configured to allow for movement of the each lower side strap 40 in a direction upward and downward.

Figure 10:
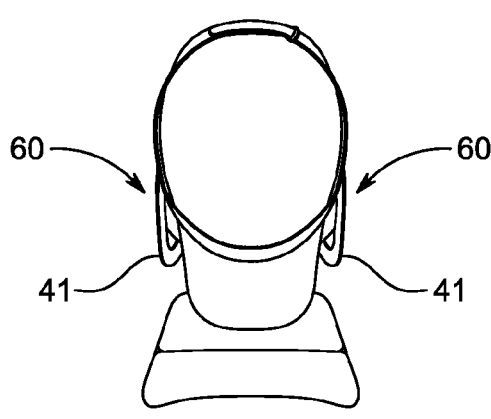
FIG. 10 shows a rear view of a headgear in an in use configuration.
Figure 10A:
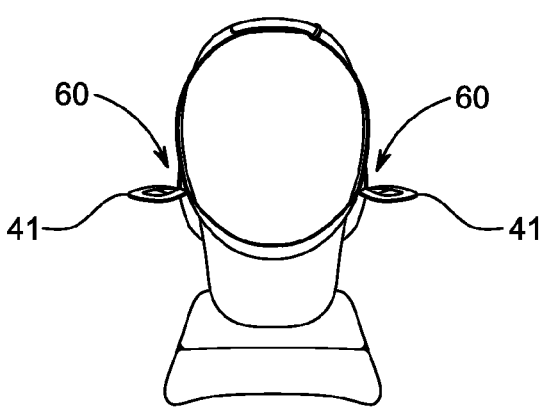
FIG. 10A shows a rear view of a headgear in an intermediate position between an in use and a donning and doffing configuration.
Figure 10B:
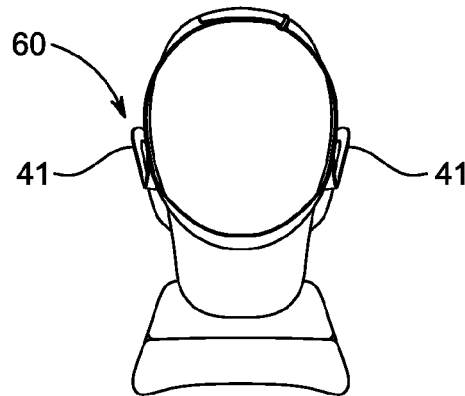
FIG. 10B shows a rear view of a headgear in a donning and doffing configuration.
Figure 11:
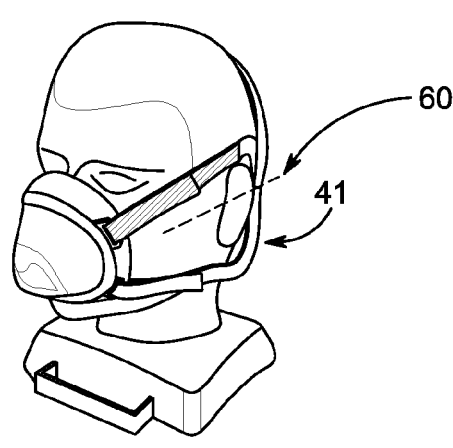
FIG. 11 shows a headgear in an in use configuration.
Figure 11A:
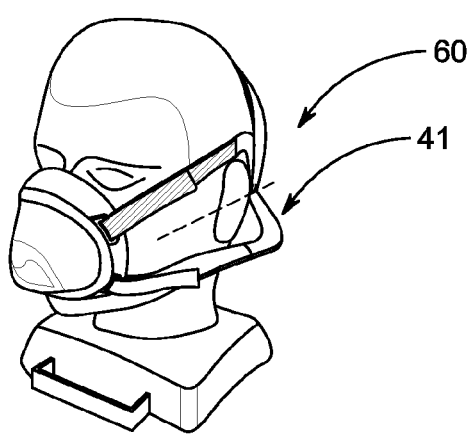
FIG. 11A shows a headgear in an intermediate position between an in use and a donning and doffing configuration.
Figure 11B:
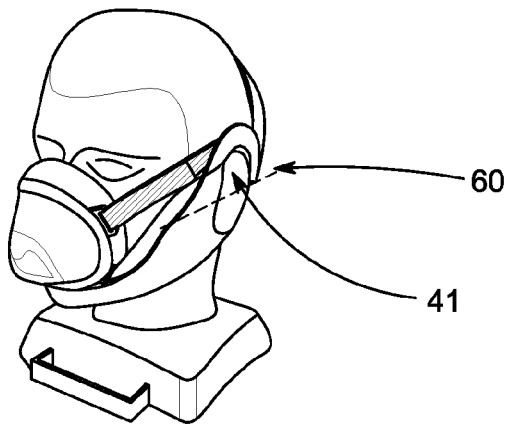
FIG. 11B shows a headgear in a donning and doffing configuration.

The pivotable connection 60 may be configured to allow for movement of the lower side strap 40 in a direction inward and outward from a side of the headgear 10 (as for example shown by FIGS. 10-10B).

The pivotable connection 60 may be configured to allow for movement of the lower side strap 40 in a direction outward from a side of a user's head (as for example shown by FIGS. 10-10B).

The pivotable connection 60 may be configured to allow for movement of the lower side strap 40 in a direction outwardly from head/headgear 10 (as for example shown by FIGS. 10-10B).

The pivotable connection 60 may be provided by a hinge, or by an elastic connection.

Figure 6:
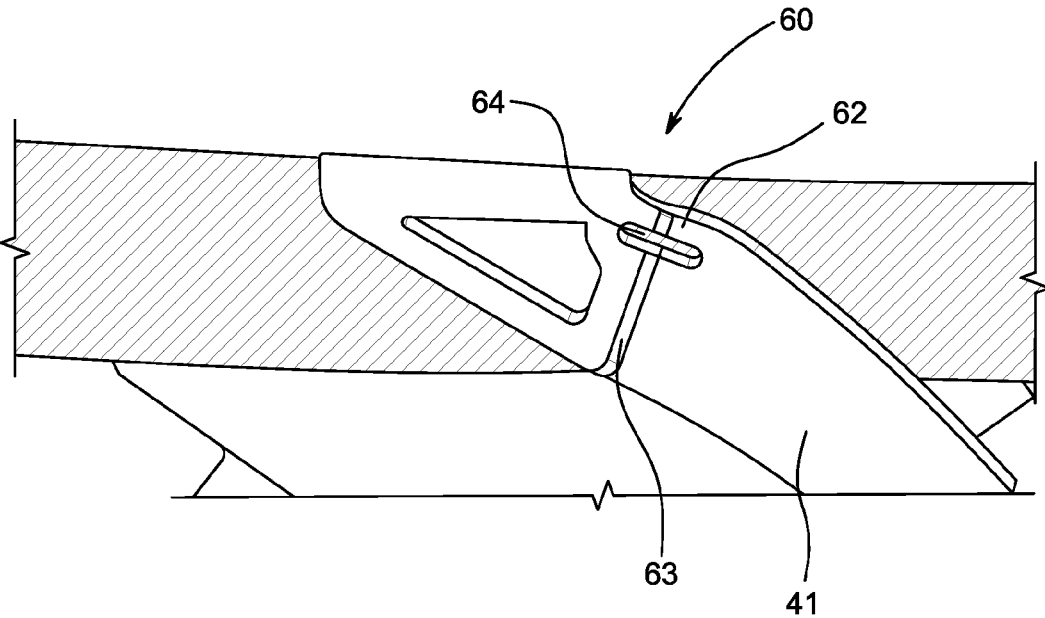
FIG. 6 shows a pivotable connection.
Figure 7:
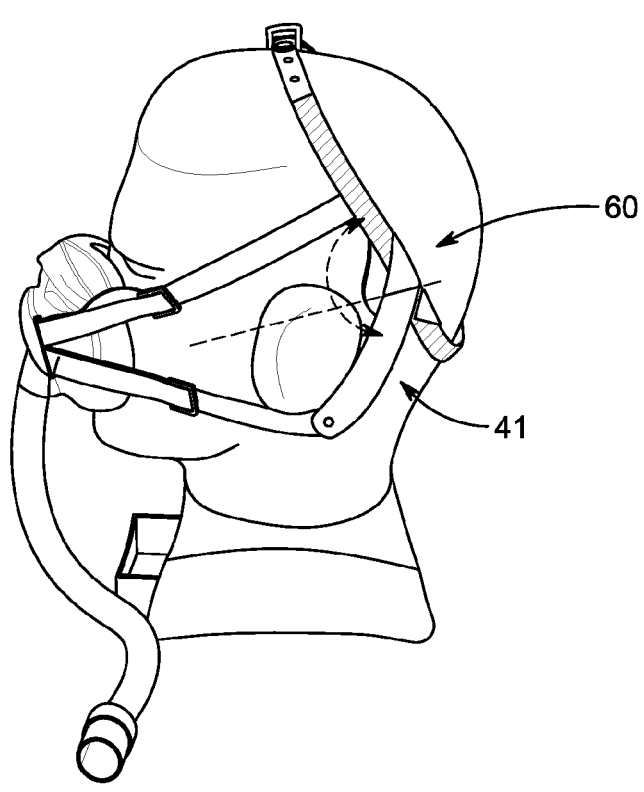
FIG. 7 shows a side view of a headgear in an in use configuration
Figure 7A:
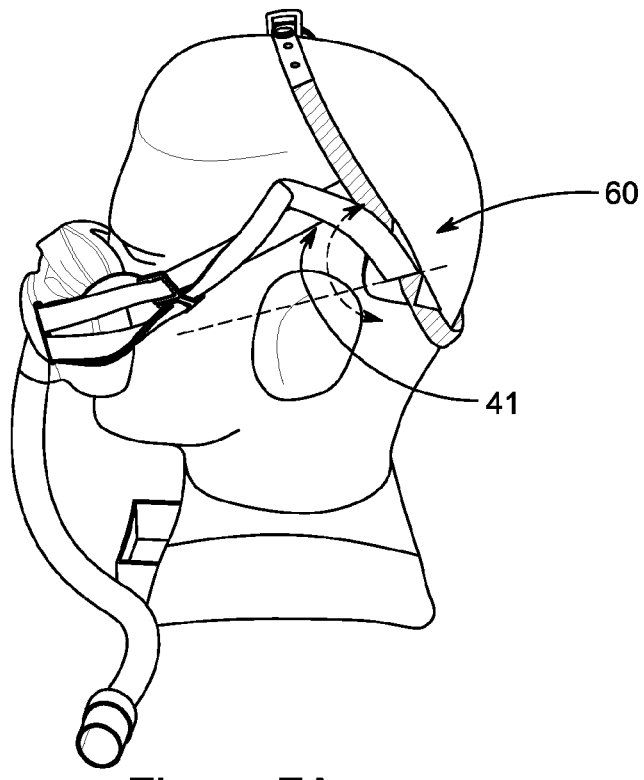
FIG. 7A shows a side view of a headgear in a donning and doffing configuration.
Figure 8:
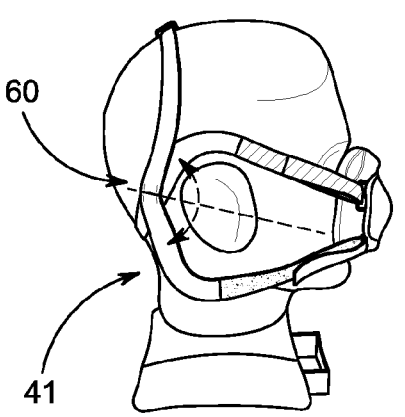
FIG. 8 shows a side view of a headgear in an in use configuration.
Figure 8A:
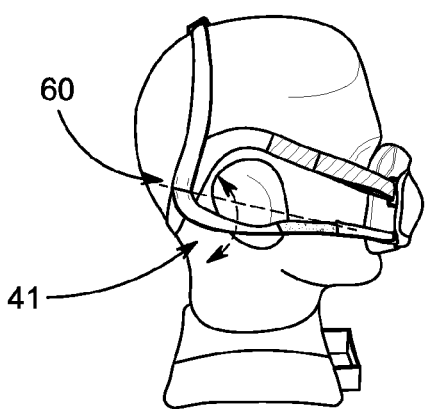
FIG. 8A shows a side view of a headgear in an intermediate position between an in use and a donning and doffing configuration.
Figure 8B:
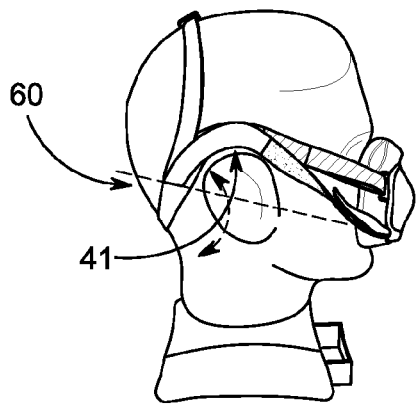
FIG. 8B shows a side view of a headgear in a donning and doffing configuration.
Figure 9:
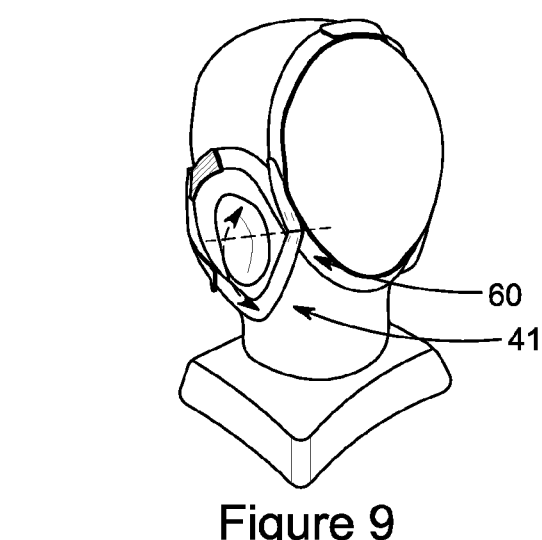
FIG. 9 shows a headgear in an in use configuration.
Figure 9A:
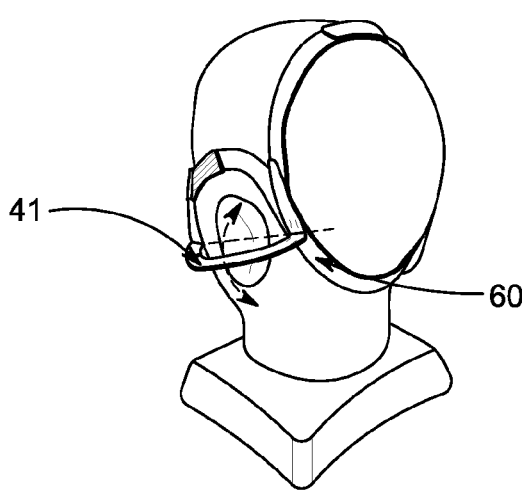
FIG. 9A shows a headgear in an intermediate position between an in use and a donning and doffing configuration.
Figure 9B:
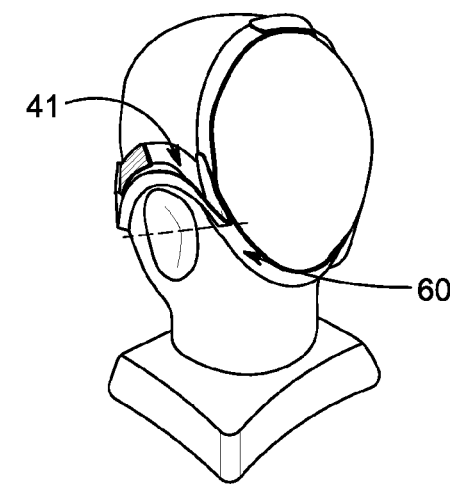
FIG. 9B shows a headgear in a donning and doffing configuration.

As shown in FIG. 6, the pivotable connection 60 may be provided for example by a living hinge. Note that FIG. 6 is a exemplary of a type of pivotable connection 60, and not necessarily the pivotable connection as shown in FIG. 5.

The pivotable connection 60 may comprise a reinforcement portion 62. The reinforcement portion 62 may be configured to be located at one side (for example as shown in FIG. 6) or both sides of the pivotable connection 60.

As illustrated by FIG. 6, the pivotable connection 60 may comprise a first living hinge portion 63 and the reinforcement portion 62. A gap 64 may be provided between the first living hinge portion 63 and the reinforcement portion 62. The gap 64 may act to decouple forces acting on the first living hinge portion 63 and the reinforcement portion 62.

The reinforcement portion 62 is provided at a location of the pivotable connection 60 (for example a living hinge as shown in FIG. 6) where the highest concentration of stress is located.

The reinforcement portion 62 increases the tear resistance of the pivotable connection 60.

The pivotable connection 60 may be provided by a localised decrease in thickness along a pivotable connection axis 61 of the pivotable connection 60. The localised decrease in thickness may be provided as part of the rear loop 20, the lower side strap 40 or the upper side strap 50.

The pivotable connection 60 may comprise a pivotable connection axis 61 about which the pivotable connection 60 pivots.

The pivotable connection 60 is configured to only pivot about the pivotable connection axis 61 and resist pivoting about other axis.

The pivotable connection 60 may be formed by a decrease in bending stiffness of the rear loop 20 or lower side strap 40 in a pivotable connection axis 61.

As shown in Figure the pivotable connection 60 is formed as part of rear strap 30 of the rear loop 20.

In some embodiments, the pivotable connection 60 may be formed as a separate component.

In some embodiments, the pivotable connection 60 may be formed as part of the lower side strap.

As shown in FIG. 2 the pivotable connection axis 61 of the pivotable connection 60 extends in a direction so as to bisect the lower side strap 40 and the upper side strap 50.

In some embodiments, the pivotable connection axis 61 of the pivotable connection 60 may be located in a direction substantially parallel to the upper side strap 50 and/or the lower side strap 40.

In some embodiments, the upper side strap 50 and the lower side strap 40 are substantially symmetrical about the pivotable connection axis 61. Alternatively, the upper side strap 50 may be disposed at a greater angle from the pivotable connection axis 61 than the lower side strap 40 or the lower side strap 40 may be disposed at a greater angle from the pivotable connection axis 61 than the upper side strap 50.

As shown in FIG. 2, the pivotable connection 60 is located behind a user's ear in use.

In some embodiments, the pivotable connection axis 61 is located, in use, behind the ear.

In some embodiments, the pivotable connection axis 61, in use, bisects the ear.

In some embodiments, the pivotable connection axis 61 is, in use, located vertically within the height of a user's ear.

The pivotable connection 60 may provide a restoring moment. The restoring moment may act to move the pivotable connection 60 to a stable configuration (as described in more detail below).

As shown for example in FIG. 2, the lower side straps 40 comprise at least one hinging arm 41. The hinging arm 41 extends behind an ear of the user in use. The hinging arm 41 extends from the rear loop 25.

The hinging arm 41 is configured to extend from the pivotable connection 60. As shown in FIG. 2 the hinging arm extends laterally of an elongate direction of the remainder of the lower side strap 40.

In some embodiments, the hinging arm 41, pivotable connection 60 and rear strap 30 of the rear loop 20 are formed as an integral component.

The hinging arm 41 extends downwardly from the rear strap 30. The hinging arm 41 may allow for an application of torque about the pivotable connection 60. The hinging arm 41 may aid in pivoting the rear strap 30 about the pivotable connection 60.

In some embodiments, the hinging arm 41 is configured to be move towards the front portion 31 of the rear strap 30 when moving to a donning and doffing configuration.

In some embodiments, the hinging arm 41 may comprise a preformed twist. The preformed twist may act to maintain the pivotable connection 60 in a stable state (as described in more detail below).

In some embodiments, an end of the hinging arm 41 located away from the pivotable connection 60 is twisted in a clockwise direction. In some embodiments, an end of the hinging arm 41 located away from the pivotable connection 60 is twisted inwardly.

The hinging arm 41 may be for example coiled to form the preformed twist.

The preformed twist may be provided in the hinging arm 41 when moulded.

FIG. 4A shows the rear loop 20, and optionally the rear strap 30 may having a pivotable connection support 36.

The pivotable connection support 36 is located, in use, between the user and the pivotable connection 60.

The pivotable connection support 36 provides an area to distribute load generated by pivoting of the pivotable connection 60. Distributing any force directed towards a patient's head from pivoting of the pivotable connection 60 increases comfort for a user. If the force is provided for example as a point load a user may experience discomfort when using the interface 1.

The headgear 10 is operable between a first configuration being an in use configuration (for example as shown in FIGS. 2, 8, 9 and 10) and a second configuration being a donning and doffing configuration (for example as shown in FIGS. 4B, 7A, 8A, 9A and 10A) by hinging of a lower side strap 40 about the pivotable connection 60.

The donning and doffing and in use configurations are described below in more detail.

The pivotable connection 60 may allow for the user to manipulate the headgear 10 into a donning and doffing configuration by movement of the headgear 10 and/or interface 1.

Figure 4B:
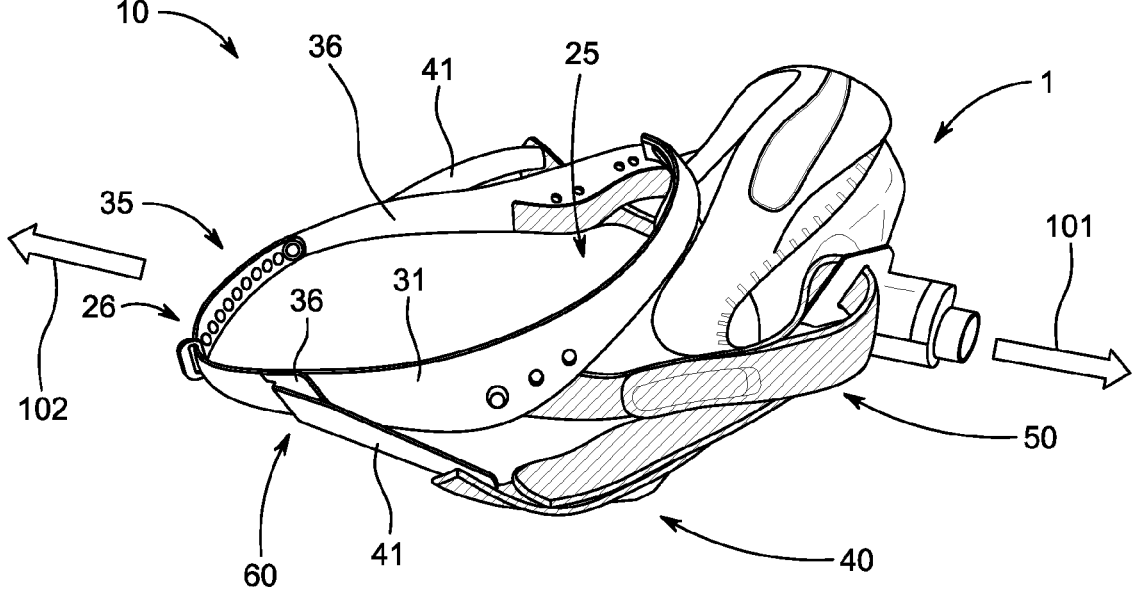
FIG. 4B shows a side view of a headgear in a donning and doffing configuration.

FIG. 4B shows a headgear 10 in a donning and doffing configuration.

In the donning and doffing configuration the pair of lower side straps 40 are located further apart than in the use configuration.

In some embodiments, in the in use configuration the lower side strap is located inward from the upper side strap In some embodiments, in the donning and doffing configuration the lower side strap is located outward from the upper side strap.

As shown in FIG. 4B, movement and/or rotation of the rear strap 35 in a direction away from the interface 1 (for example direction 100) causes the headgear 10 to enter the donning and doffing configuration.

In some embodiments, the lower side straps 40 may be manually actuated by the user about the pivotable connections.

In some embodiments, movement and/or rotation of the top strap 25 in a direction toward from the interface 1 causes the headgear 10 to enter the donning and doffing configuration.

In some embodiments, a force may be provided by a user in directions 100 and 101, to cause the headgear 10 to enter the donning and doffing configuration.

The pivotable connection 60 may allow for the user to manipulate the headgear 10 into an in use configuration by correct positioning of the interface 1 and/or headgear 10 (described in more detail below)

The headgear 10 is configured to automatically move to the in use configuration when correctly positioned on a user.

As shown in FIGS. 4D, 7, 8, 9 and 10, positioning the interface 1 and headgear 10 on a user's face causes the headgear 10 to enter the use configuration.

Figure 4C:
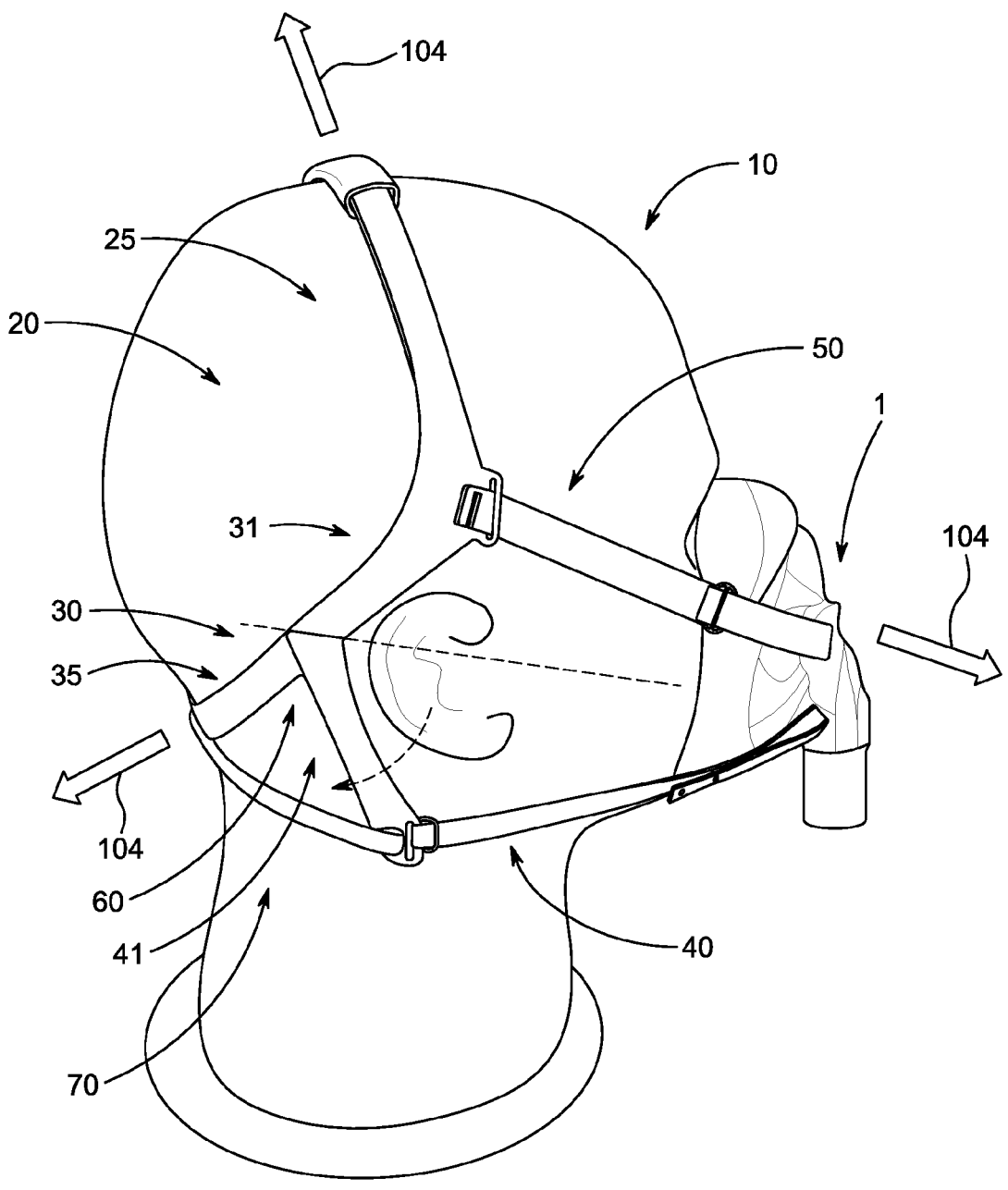
FIG. 4C shows a side view of a headgear and interface.

In some embodiments, positioning of the top strap 25 across a top of the user's head, and/or the rear strap 30 across a back of the user's head causes the headgear 10 to enter the in use configuration. For example this as shown in FIG. 4C when the headgear is placed on a user's head the pivotable connection 60 pivots so the headgear enters the the in use configuration FIG. 4C shows the application of forces 104 to the headgear to maintain the headgear in the in use configuration.

The pivotable connection 60 is configurable between the donning and doffing configuration and the in use configuration by an application of a moment about the pivotable connection 60. Application of the moment may be provided by application of any one or a combination of the forces described above, or by movement of straps of the headgear.

The pivotable connection 60 is maintained in in the use by application of a moment about the pivotable connection 60. Application of the moment may be provided by application of any one or a combination of the forces described above, or by movement of straps of the headgear.

The pivotable connection 60 is a bistable pivotable connection. The bistable pivotable connection has two configurations where the connection is in a stable state with the locations of the pivotable connection 60 between these states being unstable states.

In some embodiments the pivotable connection 60 may be a monostable pivotable connection. The monostable pivotable connection has a single state with the remainder of the locations of the pivotable connection 60 being unstable states.

Where the pivotable connection 60 is in a stable state applications of a moment about the pivotable connection 60 lower than a threshold will not cause the pivotable connection 60 to pivot from the stable state. If a moment higher than the threshold is applied about the pivotable connection 60 then the pivotable connection 60 may pivot from the stable state.

In the unstable states, an application of moment about the pivotable connection 60 will cause the pivotable connection 60 to pivot (assuming for example frictional forces are overcome).

The pivotable connection 60 has a first stable configuration where the headgear 10 is in the use configuration (for example shown in FIGS. 7, 8, 9, and 10).

As shown in FIGS. 4B, 7A, 8B, 9B and 10B the pivotable connection 60 may have a second stable configuration where the headgear 10 is in the donning and doffing configuration.

As illustrated for example In the donning and doffing configuration the pair of lower side straps 40 are located closer to the upper side straps 50 than in the use configuration.

In the in use configuration (optionally the first stable configuration) the lower side strap is provided in a position located above the lower side strap in the in donning and doffing configurations (optionally the second stable configuration.)

In some embodiments, the in donning and doffing configuration the lower side strap, or a portion of the lower side strap may be provided in a location adjacent the upper side strap.

In some embodiments, the headgear 10 comprises at least one intermediate position. The at least one intermediate position is located between the first stable configuration and the second stable configuration.

The at least one intermediate position is an unstable configuration as described in more detail above.

In some embodiments, in at least one the intermediate position the distance between the lower side straps 40 is larger than in the first stable configuration and/or the second stable configuration.

Stability of the pivotable connection 60 may be governed by the orientation of the headgear 10. In FIG. 4B the pivotable connection 60 is in a stable configuration because of the forces 100, 101 applied to the headgear 10 and interface 1. In FIGS. 7, 8, 9 and 10 the pivotable connection 60 is in a stable configuration because of the force applied to the headgear 10 by the user's head.

FIG. 5 shows an example of a pivotable connection 60 moving between a first stable configuration (indicated by reference 113), a series of intermediate positions (indicated by 111 and 111'), and a second stable configuration (indicated by reference 112). FIG. 6 shows an example of a pivotable connection 60.

Figure 12:
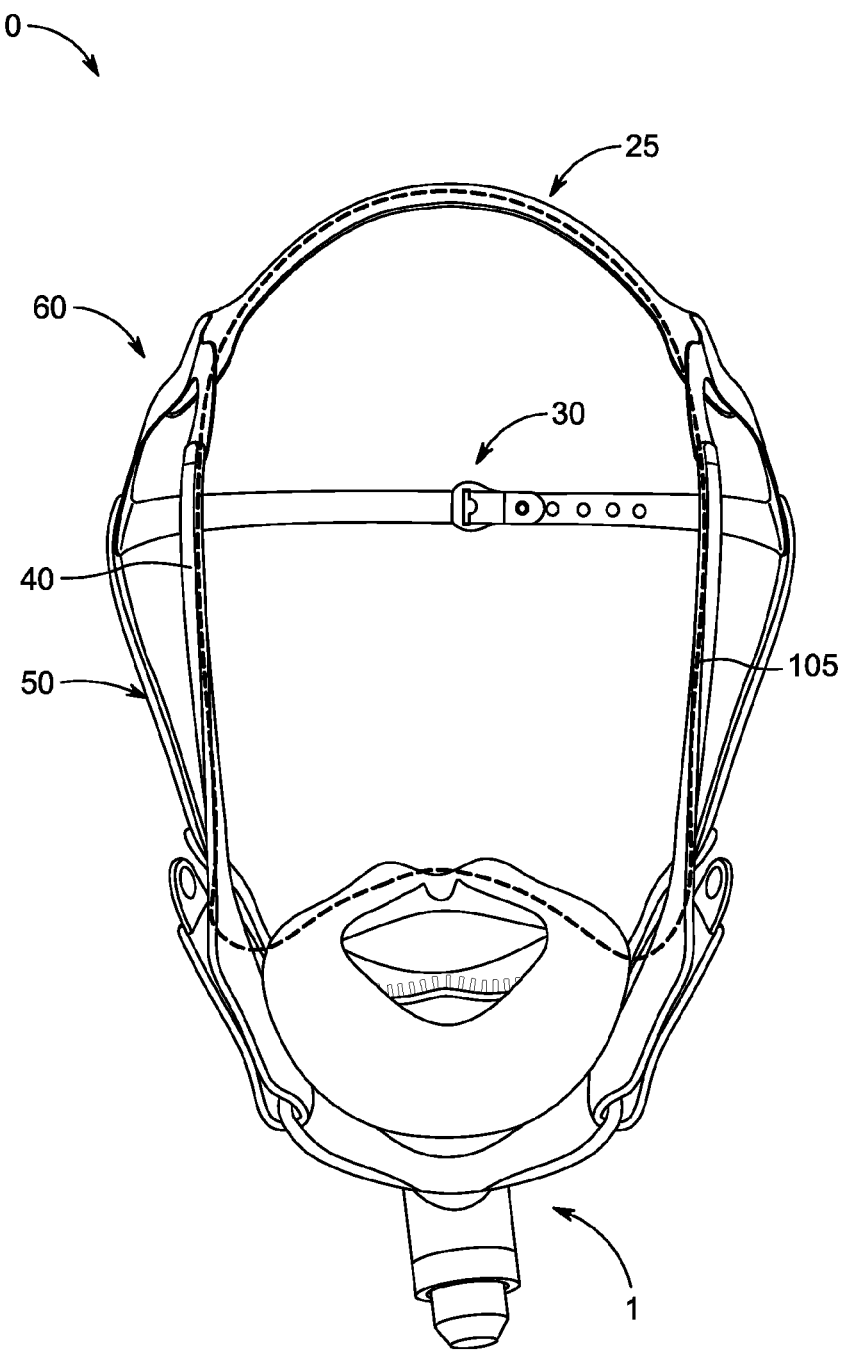
FIG. 12 shows a lower view of a headgear in an in use configuration.
Figure 13:
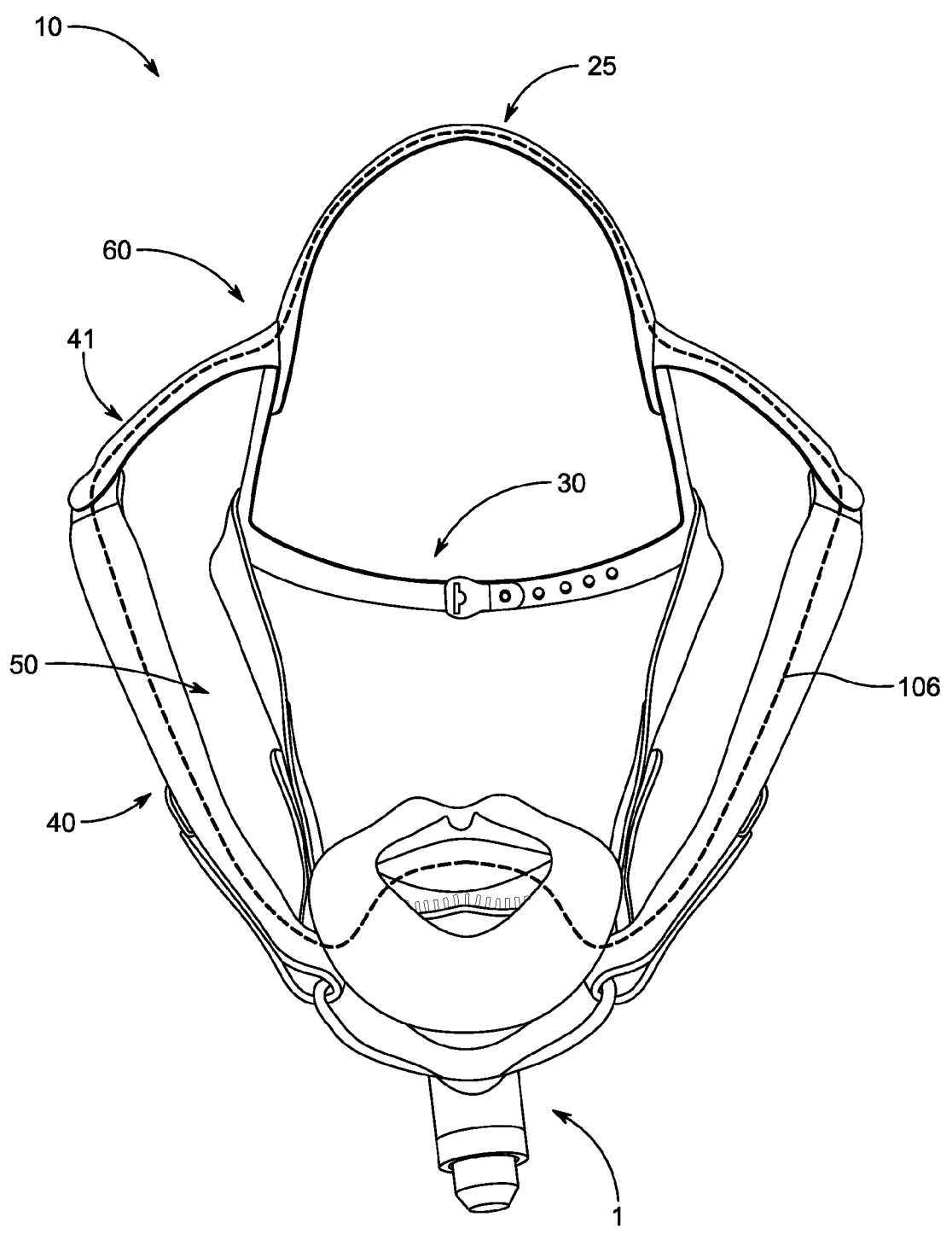
FIGS. 13 and 13A show a lower view of a headgear in a donning and doffing configuration.
Figure 13A:
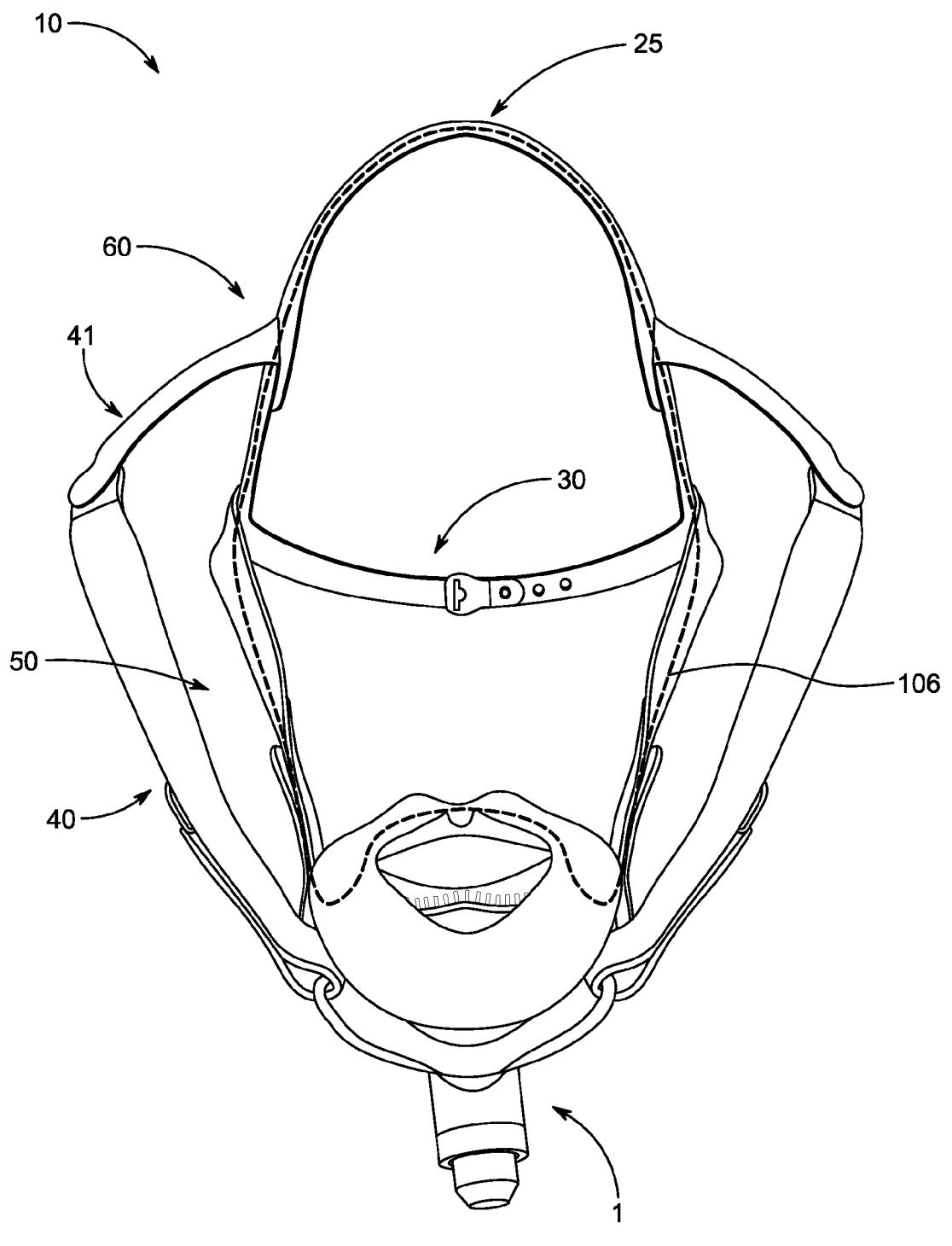

FIGS. 12, 13 and 13A show a bottom view of a headgear 10 and interface 1. FIG. 12 shows the headgear in an in use configuration (as a first configuration). FIGS. 13 and 13A shows the headgear in a donning and doffing configuration (as a second configuration).

As shown in FIG. 12, in the in use configuration the lower side strap, rear strap, and interface define a first cross-sectional area 105. Additionally or alternatively, in the in use configuration the lower side strap, rear strap, and interface define a first perimeter 105.

As shown in FIG. 13, in the in donning and doffing configuration the lower side strap, rear strap, and interface define a second cross-sectional area 106. Additionally or alternatively, in the in donning and doffing configuration the lower side strap, rear strap, and interface define a second perimeter 106.

In some embodiments, for example as shown in the embodiment of FIG. 13, in the in donning and doffing configuration the upper side straps, rear strap and interface define a second cross-sectional area 106'. Additionally or alternatively, in the in donning and doffing configuration in the in donning and doffing configuration the upper side straps, rear strap and interface define a second perimeter 106'

As shown in FIGS. 12, 13 and 13A the first cross sectional area 105 is less than the second cross sectional area 106, 106'.

As shown in FIGS. 12, 13 and 13A the first perimeter 105 is less than the second perimeter 106, 106'.

The larger available area and/or perimeter in the in the donning and doffing configuration (for example as shown in FIGS. 13 and 13A as compared to the in use configuration as shown in FIG. 12) allows for easier donning and doffing of the headgear.

The first cross-sectional area and/or a first perimeter 105 are measured from a bottom perspective of the headgear 10.

The second cross-sectional area and/or a second perimeter 106, 106' are measured from a bottom perspective of the headgear 10.

In the second configuration an opening for the head of a user to the headgear 10 is defined by the second cross sectional area.

As for example described in more detail above, the headgear is configurable between the in use configuration and the donning and doffing configuration by pivoting of each lower side strap 40 about a pivotable connection 60.

The load paths 120, 121 for distribution of forces throughout the headgear may also act to maintain the pivotable connection 60 in a stable configuration (for example the in use configuration and donning and doffing configuration).

FIG. 2 shows an example of a first load path 120, and a second load path 121 for the distribution of force in the headgear when in the in use configuration.

The first load path 120 and second load path 121 indicate the load path for the headgear when in an in use configuration.

The first load path 120 distributes forces through the upper side strap 50 to the top strap 25 and rear strap 30 of the rear loop 20.

The second load path 121 distributes forces through the lower side strap (to the hinging arm 41 if present) and to the rear portion 35 of the rear strap 30 of the rear loop 20. As discussed above the hinging arm 41 may be rigid or semi-rigid so as to transfer force to the rear portion 35 of the rear strap 30 of the rear loop 20.

In embodiments which have an elastic strap 70, the load path is configured to ensure that load on the elastic strap is minimised to instead pass force through the rear strap 30 to the rear portion 35 of the rear strap 30 of the rear loop 20.

The invention claimed is:

1. A headgear for an interface, comprising:
   a rear loop;
   a lower side strap extending from the interface to the rear loop;
   a pivotable connection, the pivotable connection located between the lower side strap and the rear loop, or on the lower side strap, wherein the pivotable connection is configured to allow for lateral movement of the lower side strap;
   wherein the pivotable connection is located behind an ear of the user in use.

2. The headgear of claim 1, wherein the pivotable connection is provided by a hinge.

3. The headgear of claim 1, wherein the pivotable connection is configured to allow for movement of the lower side strap in a direction upward and downward.

4. The headgear of claim 1, wherein the headgear is operable between a first configuration being an in use configuration and a second configuration being a donning and doffing configuration by pivoting of the lower side strap about the pivotable connection.

5. The headgear of claim 4, wherein the rear loop comprises:
   a top strap configured to extend across a top of the user's head in use,
   a rear strap configured to extend across a back of the user's head in use.

6. The headgear of claim 5, wherein the headgear comprises an upper side strap extending from an interface to the rear loop.

7. The headgear of claim 6, wherein, in use, positioning of the top strap across a top of the user's head, and/or the rear strap across a back of the user's head causes the headgear to enter the use configuration.

8. The headgear of claim 6, wherein a pivotable connection axis of the pivotable connection is located in a direction substantially parallel to the upper side strap and/or the lower side strap.

9. The headgear of claim 6, wherein a pivotable connection axis of the pivotable connection extends in a direction so as to bisect the lower side strap and the upper side strap.

10. The headgear of claim 5, wherein movement and/or rotation of the rear strap in a direction away from the interface causes the headgear to enter the donning and doffing configuration.

11. The headgear of claim 2, wherein movement and/or rotation of the top strap in a direction toward the interface causes the headgear to enter the donning and doffing configuration.

12. The headgear of claim 5, wherein the rear strap comprises a pivotable connection support.

13. The headgear of claim 12, wherein the pivotable connection support located, in use, between the user and the pivotable connection.

14. The headgear of claim 12, wherein the pivotable connection support providing an area to distribute load generated by hinging.

15. The headgear of claim 5, wherein the headgear comprises a pair of upper side straps and a pair of lower side straps, each upper and lower side strap pair being located on each side of the headgear.

16. The headgear of claim 15, wherein in the donning and doffing configuration the pair of lower side straps are located further apart than in the use configuration.

17. The headgear of claim 15, wherein the lower side straps comprise at least one hinging arm, the hinging arm configured to extend behind the ear of the user in use.

18. The headgear of claim 17, wherein the hinging arm extends downwardly from the rear strap.

19. The headgear of claim 17, wherein the hinging arm comprises a preformed twist, wherein an end of the hinging arm located away from the pivotable connection is twisted inwardly.

20. The headgear of claim 15, wherein the headgear comprises a pair of pivotable connections, each pivotable connection located between the upper side strap and lower side strap of each upper and lower side strap pair, or on the each lower side strap.

21. The headgear of claim 20, wherein in the donning and doffing configuration the pair of lower side straps are located closer to the upper side straps than in the use configuration.

22. The headgear of claim 5, wherein the pivotable connection is located at a connection point between the lower side strap and the rear strap.

23. The headgear of claim 4, wherein, in use, positioning of the interface on a user's face causes the headgear to enter the use configuration.

24. A headgear for an interface, comprising:
a rear loop;
a lower side strap extending from the interface to the rear loop;
a pivotable connection, the pivotable connection located between the lower side strap and the rear loop, or on the lower side strap, wherein the pivotable connection is configured to allow for lateral movement of the lower side strap;
wherein the headgear is operable between a first configuration being an in use configuration and a second configuration being a donning and doffing configuration by pivoting of the lower side strap about the pivotable connection;
wherein the pivotable connection is a bistable pivotable connection, having a first stable configuration where the headgear is in the use configuration, and a second stable configuration where the headgear is in the donning and doffing configuration.

25. The headgear of claim 24, wherein the headgear comprises an intermediate position, wherein the intermediate position is located between the first stable configuration and the second stable configuration.

26. The headgear of claim 25, wherein the intermediate position is an unstable configuration.

27. The headgear of claim 25, wherein the headgear comprises a pair of upper side straps and a pair of lower side straps including the lower side strap, each upper and lower side strap pair being located on each side of the headgear, wherein in the intermediate position the distance between the lower side straps is larger than in the first stable configuration and/or the second stable configuration.

28. A headgear for an interface, comprising:
a rear loop;
a lower side strap extending from the interface to the rear loop;
an upper side strap extending from an interface to the rear loop;
a pivotable connection, the pivotable connection located between the lower side strap and the rear loop, or on the lower side strap, wherein the pivotable connection is configured to allow for lateral movement of the lower side strap;
wherein the upper side strap and the lower side strap are substantially symmetrical about a pivotable connection axis.

* * * * *